(12) United States Patent
Fischer et al.

(10) Patent No.: US 11,041,216 B2
(45) Date of Patent: *Jun. 22, 2021

(54) COMPOSITIONS AND METHODS FOR DETECTING AND QUANTIFYING NUCLEIC ACID SEQUENCES IN BLOOD SAMPLES

(71) Applicant: Longhorn Vaccines and Diagnostics, LLC, Bethesda, MD (US)

(72) Inventors: Jeffrey D. Fischer, Washington, DC (US); Luke T. Daum, San Antonio, TX (US); Gerald W. Fischer, Bethesda, MD (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 542 days.

This patent is subject to a terminal disclaimer.

(21) Appl. No.: 15/361,228

(22) Filed: Nov. 25, 2016

(65) Prior Publication Data

US 2017/0073738 A1 Mar. 16, 2017

Related U.S. Application Data

(63) Continuation-in-part of application No. 14/048,875, filed on Oct. 8, 2013, now abandoned, which is a continuation-in-part of application No. 13/094,809, filed on Apr. 26, 2011, now Pat. No. 8,652,782, which is a continuation-in-part of application No. 12/916,263, filed on Oct. 29, 2010, now abandoned, and a continuation-in-part of application No. 12/510,968, filed on Jul. 28, 2009, now Pat. No. 8,097,419, and a continuation-in-part of application No. 12/426,890, filed on Apr. 20, 2009, now Pat. No. 8,080,645, and a continuation-in-part of application No. 12/243,949, filed on Oct. 1, 2008, now Pat. No. 8,084,443, application No. 15/361,228, filed on Nov. 25, 2016, which is a continuation-in-part of application No. 14/527,281, filed on Oct. 29, 2014, now Pat. No. 9,598,737, and a continuation-in-part of application No. 13/890,512, filed on May 9, 2013, now Pat. No. 9,365,904, application No. 15/361,228, filed on Nov. 25, 2016, which is a continuation-in-part of application No. PCT/US2015/032432, filed on May 26, 2015.

(60) Provisional application No. 62/260,064, filed on Nov. 25, 2015, provisional application No. 60/976,728, filed on Oct. 1, 2007, provisional application No. 61/897,015, filed on Oct. 29, 2013, provisional application No. 61/737,250, filed on Dec. 14, 2012, provisional application No. 61/695,960, filed on Aug. 31, 2012, provisional application No. 61/646,060, (Continued)

(51) Int. Cl.
C12Q 1/68 (2018.01)
C12N 15/10 (2006.01)
C12Q 1/70 (2006.01)
C12Q 1/689 (2018.01)
C12Q 1/6806 (2018.01)

(52) U.S. Cl.
CPC ......... *C12Q 1/689* (2013.01); *C12N 15/1003* (2013.01); *C12Q 1/6806* (2013.01); *C12Q 1/701* (2013.01); *C12Q 2600/16* (2013.01); *C12Q 2600/166* (2013.01)

(58) Field of Classification Search
CPC .................................................. C12Q 1/689
See application file for complete search history.

(56) References Cited

U.S. PATENT DOCUMENTS 1,307,416 A 6/1919 Pine
2,697,373 A 12/1954 Siekmann
(Continued)

FOREIGN PATENT DOCUMENTS

CN 1310235 8/2001
EP 0313224 4/1989
(Continued)

OTHER PUBLICATIONS

Corless CE, Guiver M, Borrow R, Edwards-Jones V, Fox AJ, Kaczmarski EB. Simultaneous detection of Neisseria meningitidis, Haemophilus influenzae, and *Streptococcus pneumoniae* in suspected cases of meningitis and septicemia using real-time PCR. J Clin Microbiol. Apr. 2001; 39(4): 1553-8 (Year: 2001).*

(Continued)

*Primary Examiner* — Teresa E Strzelecka
*Assistant Examiner* — Olayinka A Oyeyemi
(74) *Attorney, Agent, or Firm* — Remenick PLLC

(57) ABSTRACT

The invention is directed to compositions and methods for rapidly detecting, amplifying, and quantitating one or more pathogen-specific nucleic acids in a biological sample, and in particular, samples obtained from patients with sepsis. The invention also provides diagnostic kits containing specific amplification primers, and labeled detection probes that specifically bind to the amplification products obtained therefrom. The invention is also directed to detecting the quantity or ratio of genomic sequences and mRNA sequences of an individual suspected of being infected with an infectious agent over time to assess the progress of the infection over time. Also disclosed are compositions and methods for the isolation and characterization of nucleic acids that are specific to one or more pathogens, such as, for example, Influenza virus, *Mycobacterium tuberculosis, Plasmodium*, and/or HIV from a wide variety of samples including those of biological, environmental, clinical and/or veterinary origin.

37 Claims, 2 Drawing Sheets

Related U.S. Application Data filed on May 11, 2012, provisional application No. 61/644,876, filed on May 9, 2012, provisional application No. 62/003,976, filed on May 28, 2014.

(56) References Cited

U.S. PATENT DOCUMENTS

| | | |
|---|---|---|
| 4,116,777 A | 9/1978 | Takatsy et al. |
| 4,196,265 A | 4/1980 | Koprowski et al. |
| 4,235,244 A | 11/1980 | Abele et al. |
| 4,315,073 A | 2/1982 | Brown et al. |
| 4,355,102 A | 10/1982 | Quash |
| 4,356,170 A | 10/1982 | Jennings et al. |
| 4,371,091 A | 2/1983 | Gelina |
| 4,372,945 A | 2/1983 | Likhite |
| 4,474,757 A | 10/1984 | Arnon et al. |
| 4,529,702 A | 7/1985 | Bryan |
| 4,554,101 A | 11/1985 | Hopp |
| 4,559,231 A | 12/1985 | Bjerre et al. |
| 4,578,770 A | 3/1986 | Mitani |
| 4,588,680 A | 5/1986 | Bucher et al. |
| 4,596,792 A | 6/1986 | Vyas |
| 4,599,230 A | 7/1986 | Milich et al. |
| 4,601,903 A | 7/1986 | Frasch |
| 4,608,251 A | 8/1986 | Mia |
| 4,634,664 A | 1/1987 | Oestberg |
| 4,634,666 A | 1/1987 | Engleman et al. |
| 4,668,476 A | 5/1987 | Bridgham et al. |
| 4,683,195 A | 7/1987 | Mullis et al. |
| 4,683,202 A | 7/1987 | Mullis |
| 4,707,450 A | 11/1987 | Nason |
| 4,744,982 A | 5/1988 | Hunter et al. |
| 4,746,490 A | 5/1988 | Saneii |
| 4,749,490 A | 6/1988 | Smyth et al. |
| 4,800,159 A | 1/1989 | Mullis et al. |
| 4,803,998 A | 2/1989 | Kezes et al. |
| 4,816,513 A | 3/1989 | Bridgham et al. |
| 4,883,750 A | 11/1989 | Whiteley et al. |
| 4,954,449 A | 9/1990 | Hunter et al. |
| 4,981,782 A | 1/1991 | Judd et al. |
| 4,996,143 A | 2/1991 | Heller et al. |
| 5,091,316 A | 2/1992 | Monthony et al. |
| 5,108,927 A | 4/1992 | Dorn |
| 5,136,019 A | 8/1992 | Judd et al. |
| 5,145,684 A | 9/1992 | Liversidge et al. |
| 5,149,653 A | 9/1992 | Roser |
| 5,163,441 A | 11/1992 | Monthony et al. |
| 5,168,039 A | 12/1992 | Crawford et al. |
| 5,182,109 A | 1/1993 | Tamura et al. |
| 5,186,898 A | 2/1993 | Bridgham et al. |
| 5,187,060 A | 2/1993 | Cerutti et al. |
| 5,234,809 A | 8/1993 | Boom et al. |
| 5,243,030 A | 9/1993 | Judd et al. |
| 5,252,458 A | 10/1993 | Liav et al. |
| 5,290,686 A | 3/1994 | Kendal et al. |
| 5,316,910 A | 5/1994 | Rota et al. |
| 5,370,998 A | 12/1994 | Crawford et al. |
| 5,399,363 A | 3/1995 | Liversidge et al. |
| 5,482,856 A | 1/1996 | Fell, Jr. et al. |
| 5,503,841 A | 4/1996 | Doyle et al. |
| 5,543,158 A | 8/1996 | Gref et al. |
| 5,545,555 A | 8/1996 | Racioppi et al. |
| 5,552,157 A | 9/1996 | Yagi et al. |
| 5,565,213 A | 10/1996 | Nakamori et al. |
| 5,565,322 A | 10/1996 | Heller |
| 5,567,434 A | 10/1996 | Szoka, Jr. |
| 5,571,511 A | 11/1996 | Fischer |
| 5,589,174 A | 12/1996 | Okuno et al. |
| 5,627,071 A | 5/1997 | Triva |
| 5,631,350 A | 5/1997 | Okuno et al. |
| 5,641,515 A | 6/1997 | Ramtoola |
| 5,656,016 A | 8/1997 | Ogden |
| 5,663,055 A | 9/1997 | Turner et al. |
| 5,679,356 A | 10/1997 | Bonnem et al. |
| 5,691,299 A | 11/1997 | Fabry |
| 5,697,899 A | 12/1997 | Hillman et al. |
| 5,702,944 A | 12/1997 | Racioppi et al. |
| 5,719,020 A | 2/1998 | Liav et al. |
| 5,736,333 A | 4/1998 | Livak et al. |
| 5,738,868 A | 4/1998 | Shinkarenko |
| 5,741,516 A | 4/1998 | Webb et al. |
| 5,766,841 A | 6/1998 | Liav et al. |
| 5,770,219 A | 6/1998 | Chiang et al. |
| 5,779,708 A | 7/1998 | Wu |
| 5,783,208 A | 7/1998 | Venkateshwaran et al. |
| 5,785,975 A | 7/1998 | Parikh |
| 5,795,582 A | 8/1998 | Wright |
| 5,795,587 A | 8/1998 | Gao et al. |
| 5,797,898 A | 8/1998 | Santini, Jr. et al. |
| 5,800,810 A | 9/1998 | Doyle et al. |
| 5,849,489 A | 12/1998 | Heller |
| 5,891,624 A | 4/1999 | Huang |
| 5,945,515 A | 8/1999 | Chomczynski |
| 5,955,074 A | 9/1999 | Fischer |
| 5,958,379 A | 9/1999 | Regenold et al. |
| 6,015,664 A | 1/2000 | Henrickson et al. |
| 6,033,673 A | 3/2000 | Clements |
| 6,060,068 A | 5/2000 | Doyle et al. |
| 6,136,585 A | 10/2000 | Ball et al. |
| 6,162,603 A | 12/2000 | Heller |
| 6,168,915 B1 | 1/2001 | Scholl et al. |
| 6,242,582 B1 | 6/2001 | Reece et al. |
| 6,280,928 B1 | 8/2001 | Scholl et al. |
| 6,306,404 B1 | 10/2001 | LaPosta et al. |
| 6,306,582 B1 | 10/2001 | Scholl et al. |
| 6,312,395 B1 | 11/2001 | Tripp et al. |
| 6,376,172 B1 | 4/2002 | Scholl et al. |
| 6,406,842 B2 | 6/2002 | Scholl et al. |
| 6,440,423 B1 | 8/2002 | Clements et al. |
| 6,451,325 B1 | 9/2002 | Van Nest et al. |
| 6,458,577 B1 | 10/2002 | Huang |
| 6,495,316 B1 | 12/2002 | Scholl et al. |
| 6,500,432 B1 | 12/2002 | Dalemans et al. |
| 6,503,745 B1 | 1/2003 | Chand et al. |
| 6,534,065 B1 | 3/2003 | Makin et al. |
| 6,572,866 B1 | 6/2003 | Torcia |
| 6,573,080 B2 | 6/2003 | Scholl et al. |
| 6,602,510 B1 | 8/2003 | Fikes et al. |
| 6,603,908 B2 | 8/2003 | Dallas et al. |
| 6,603,998 B1 | 8/2003 | King et al. |
| 6,610,293 B1 | 8/2003 | Fischer et al. |
| 6,610,474 B1 | 8/2003 | Huang |
| 6,627,396 B1 | 9/2003 | Swanson et al. |
| 6,632,432 B1 | 10/2003 | Fischer |
| 6,680,308 B1 | 1/2004 | Hassan |
| 6,689,363 B1 | 2/2004 | Sette et al. |
| 6,713,068 B1 | 3/2004 | Audonnet et al. |
| 6,720,409 B2 | 4/2004 | Okuno et al. |
| 6,734,292 B1 | 5/2004 | Omura et al. |
| 6,759,241 B1 | 7/2004 | Hone et al. |
| 6,780,421 B1 | 8/2004 | Haensler et al. |
| 6,793,928 B1 | 9/2004 | van Scharrenburg et al. |
| 6,811,971 B2 | 11/2004 | Klepp et al. |
| 6,855,321 B1 | 2/2005 | Rappuoli et al. |
| 6,875,600 B2 | 4/2005 | Scholl et al. |
| 6,881,835 B2 | 4/2005 | Bai et al. |
| 6,893,814 B2 | 5/2005 | Swanson et al. |
| 6,939,543 B2 | 9/2005 | Fischer et al. |
| 6,946,291 B2 | 9/2005 | Scholl et al. |
| 7,090,853 B2 | 8/2006 | Kapp et al. |
| 7,223,409 B2 | 5/2007 | Nagata et al. |
| 7,279,162 B1 | 10/2007 | Fischer |
| 7,311,671 B2 | 12/2007 | Jung et al. |
| 7,351,413 B2 | 4/2008 | Page et al. |
| 7,357,936 B1 | 4/2008 | Garcon |
| 7,361,352 B2 | 4/2008 | Birkett et al. |
| 7,494,771 B2 | 2/2009 | Picard et al. |
| 7,541,194 B2 | 6/2009 | Mink et al. |
| 7,648,681 B2 | 1/2010 | Meyer et al. |
| 7,718,402 B2 | 5/2010 | Gayral et al. |
| 7,767,804 B2 | 8/2010 | Bair, Jr. et al. |
| 7,794,001 B2 | 9/2010 | Blackwell et al. |
| 8,080,645 B2* | 12/2011 | Fischer ............... C12Q 1/6806 536/23.1 |

(56) References Cited

U.S. PATENT DOCUMENTS

| | | | |
|---|---|---|---|
| 8,084,443 B2* | 12/2011 | Fischer | C12Q 1/6806 514/75 |
| 8,097,419 B2 | 1/2012 | Fischer et al. | |
| 8,293,467 B2 | 10/2012 | Fischer et al. | |
| 9,481,912 B2* | 11/2016 | Fischer | C12Q 1/6806 |
| 9,598,737 B2* | 3/2017 | Daum | C12Q 1/6869 |
| 9,683,256 B2* | 6/2017 | Fischer | C12N 15/1003 |
| 9,976,136 B2* | 5/2018 | Fischer | C12Q 1/686 |
| 2001/0021501 A1 | 9/2001 | Scholl et al. | |
| 2001/0023065 A1 | 9/2001 | Lee | |
| 2001/0034022 A1 | 10/2001 | Scholl et al. | |
| 2001/0036628 A1 | 11/2001 | Scholl et al. | |
| 2002/0054882 A1 | 5/2002 | Okuno et al. | |
| 2002/0055094 A1 | 5/2002 | Reece et al. | |
| 2002/0081567 A1 | 6/2002 | Henrickson et al. | |
| 2002/0082395 A1 | 6/2002 | Fischer et al. | |
| 2002/0169140 A1 | 11/2002 | Prendergast | |
| 2003/0119209 A1 | 6/2003 | Kaylor et al. | |
| 2003/0143566 A1 | 7/2003 | Helftenbein | |
| 2003/0203357 A1 | 10/2003 | Huang | |
| 2003/0215796 A1 | 11/2003 | Scholl et al. | |
| 2003/0219442 A1 | 11/2003 | Mikayama et al. | |
| 2004/0009126 A1 | 1/2004 | Pilkiewicz et al. | |
| 2004/0013673 A1 | 1/2004 | Fischer et al. | |
| 2004/0071757 A1 | 4/2004 | Rolf | |
| 2004/0082549 A1 | 4/2004 | Jomaa | |
| 2004/0086849 A1 | 5/2004 | Shimasaki et al. | |
| 2004/0101869 A1 | 5/2004 | Berg et al. | |
| 2004/0126789 A1 | 7/2004 | Park et al. | |
| 2004/0142319 A1 | 7/2004 | Park et al. | |
| 2004/0170965 A1 | 9/2004 | Scholl et al. | |
| 2004/0214272 A1 | 10/2004 | La Rosa et al. | |
| 2004/0223976 A1 | 11/2004 | Bianchi et al. | |
| 2005/0009008 A1 | 1/2005 | Robinson et al. | |
| 2005/0042229 A1 | 2/2005 | Yang et al. | |
| 2005/0090009 A1 | 4/2005 | Cormier et al. | |
| 2005/0112656 A1 | 5/2005 | Iwaki | |
| 2005/0169941 A1 | 8/2005 | Lees | |
| 2005/0170334 A1 | 8/2005 | Mikayama et al. | |
| 2005/0181357 A1 | 8/2005 | Mikayama et al. | |
| 2005/0187213 A1 | 8/2005 | Peiris et al. | |
| 2005/0227225 A1 | 10/2005 | Krevolin | |
| 2005/0227269 A1 | 10/2005 | Lloyd, Jr. et al. | |
| 2006/0002939 A1 | 1/2006 | Fischer et al. | |
| 2006/0014185 A1 | 1/2006 | Ollikka et al. | |
| 2006/0105468 A1 | 5/2006 | Winkler et al. | |
| 2006/0121468 A1 | 6/2006 | Allnutt et al. | |
| 2006/0134648 A1 | 6/2006 | Chou et al. | |
| 2006/0147944 A1 | 7/2006 | Chomczynski | |
| 2006/0286557 A1 | 12/2006 | Basehore et al. | |
| 2007/0042358 A1 | 2/2007 | Shah | |
| 2007/0078025 A1 | 4/2007 | Pepe | |
| 2007/0102946 A1 | 5/2007 | Blackwell et al. | |
| 2007/0172835 A1 | 7/2007 | McBride et al. | |
| 2007/0196388 A1 | 8/2007 | Dowling et al. | |
| 2007/0202497 A1 | 8/2007 | Dowling et al. | |
| 2007/0202511 A1 | 8/2007 | Renuart et al. | |
| 2007/0286871 A1 | 12/2007 | Hickle et al. | |
| 2008/0032921 A1 | 2/2008 | Alexander et al. | |
| 2008/0050737 A1 | 2/2008 | Ariel et al. | |
| 2008/0069821 A1 | 3/2008 | Yang et al. | |
| 2008/0074521 A1 | 3/2008 | Olsen | |
| 2008/0075708 A1 | 3/2008 | Yu et al. | |
| 2008/0078499 A1 | 4/2008 | Feeney | |
| 2008/0107665 A1 | 5/2008 | Suckow et al. | |
| 2008/0107687 A1 | 5/2008 | Poule | |
| 2008/0118531 A1 | 5/2008 | Hoffmann et al. | |
| 2008/0139789 A1 | 6/2008 | Fischer | |
| 2008/0145373 A1 | 6/2008 | Arumugham et al. | |
| 2008/0181914 A1 | 7/2008 | Eichhorn | |
| 2008/0260763 A1 | 10/2008 | Felgner et al. | |
| 2008/0286769 A1 | 11/2008 | Stenman et al. | |
| 2009/0081202 A1 | 3/2009 | Fischer et al. | |
| 2009/0098527 A1 | 4/2009 | Fischer et al. | |
| 2009/0233309 A1* | 9/2009 | Fischer | C12Q 1/6806 435/6.18 |
| 2009/0312285 A1 | 12/2009 | Fischer et al. | |
| 2010/0009343 A1 | 1/2010 | Fischer | |
| 2010/0043546 A1 | 2/2010 | Kandori et al. | |
| 2010/0055672 A1 | 3/2010 | Saghbini | |
| 2010/0151477 A1 | 6/2010 | Cawthon | |
| 2010/0221822 A1 | 9/2010 | Fischer et al. | |
| 2010/0311739 A1 | 12/2010 | Gunaratnam et al. | |
| 2011/0159497 A1 | 6/2011 | Lee et al. | |
| 2011/0281754 A1 | 11/2011 | Fischer et al. | |
| 2012/0088231 A1 | 4/2012 | Fischer et al. | |
| 2012/0100529 A1 | 4/2012 | Fischer et al. | |
| 2012/0107799 A1 | 5/2012 | Daum | |
| 2012/0115126 A1 | 5/2012 | Fischer et al. | |
| 2012/0244527 A1 | 9/2012 | Trinh et al. | |
| 2013/0260369 A1* | 10/2013 | Fischer | C12N 15/1003 435/5 |
| 2014/0030703 A1 | 1/2014 | Fischer et al. | |
| 2015/0056609 A1* | 2/2015 | Daum | C12Q 1/6869 435/5 |
| 2015/0152485 A1 | 6/2015 | Karakousis et al. | |
| 2016/0108463 A1* | 4/2016 | Fischer | C12N 15/1003 506/9 |
| 2016/0333339 A1* | 11/2016 | Fischer | C12Q 1/686 |
| 2017/0073738 A1* | 3/2017 | Fischer | C12N 15/1003 |

FOREIGN PATENT DOCUMENTS

| | | |
|---|---|---|
| EP | 0621339 | 10/1994 |
| EP | 0675199 | 10/1995 |
| EP | 0726316 | 8/1996 |
| EP | 1081496 | 3/2001 |
| JP | 2002501368 | 1/2002 |
| JP | 2003052380 | 2/2003 |
| JP | 2007519613 | 7/2007 |
| JP | 2011508742 | 3/2011 |
| RU | 2150281 | 6/2000 |
| WO | WO 91/02740 | 3/1991 |
| WO | WO1992016619 | 1/1992 |
| WO | WO1992003454 | 5/1992 |
| WO | WO1994009035 | 4/1994 |
| WO | WO1994017106 | 4/1994 |
| WO | WO1997005248 | 2/1997 |
| WO | WO 1998/40099 | 9/1998 |
| WO | WO2003026567 | 3/2003 |
| WO | WO2003053462 | 7/2003 |
| WO | WO03/095646 | 11/2003 |
| WO | WO2004002451 | 1/2004 |
| WO | WO2004004658 | 1/2004 |
| WO | WO2004043407 | 5/2004 |
| WO | WO2004055205 | 7/2004 |
| WO | WO2004072270 | 8/2004 |
| WO | WO2004084876 | 10/2004 |
| WO | WO2005010186 | 2/2005 |
| WO | WO 2005/042784 | 5/2005 |
| WO | WO2005075642 | 8/2005 |
| WO | WO2005085274 | 9/2005 |
| WO | WO2006041933 | 4/2006 |
| WO | WO2006138444 | 12/2006 |
| WO | WO2007051036 | 5/2007 |
| WO | WO2007056266 | 5/2007 |
| WO | WO2007091030 | 8/2007 |
| WO | WO2007133682 | 11/2007 |
| WO | WO2008079463 | 7/2008 |
| WO | WO2009085355 | 7/2009 |
| WO | WO2010009398 | 1/2010 |
| WO | WO2010/123908 | 10/2010 |
| WO | WO 2015/066174 | 5/2015 |

OTHER PUBLICATIONS

Sirigireddy KR, Ganta RR. Multiplex detection of Ehrlichia and Anaplasma species pathogens in peripheral blood by real-time reverse transcriptase-polymerase chain reaction. J Mol Diagn. May 2005; 7(2):308-16. (Year: 2005).*

(56) References Cited

OTHER PUBLICATIONS

Faul JL, Doyle RL, Kao PN, Ruoss SJ. Tick-borne pulmonary disease: update on diagnosis and management. Chest. Jul. 1999; 116 (1):222-30. (Year: 1999).*
Harrus S, Waner T, Aizenberg I, Bark H. Therapeutic effect of doxycycline in experimental subclinical canine monocytic ehrlichiosis: evaluation of a 6-week course. J Clin Microbiol. Jul. 1998; 36(7):2140-2 (Year: 1998).*
Wallet F, Nseir S, Baumann L, Herwegh S, Sendid B, Boulo M, Roussel-Delvallez M, Durocher AV, Courcol RJ. Preliminary clinical study using a multiplex real-time PCR test for the detection of bacterial and fungal DNA directly in blood. Clin Microbiol Infect. Jun. 2010; 16(6):774-9. Epub Aug. 18, 2009. (Year: 2009).*
Yang YG, Kim JY, Song YH, Kim DS. A novel buffer system, AnyDirect, can improve polymerase chain reaction from whole blood without DNA isolation. Clin Chim Acta. May 1, 2007; 380(1-2):112-7. Epub Jan. 30, 2007 (Year: 2007).*
García-Quintanilla A, González-Martín J, Tudó G, Espasa M, Jiménez de Anta MT. Simultaneous identification of *Mycobacterium* genus and *Mycobacterium tuberculosis* complex in clinical samples by 5'-exonuclease fluorogenic PCR. J Clin Microbiol. Dec. 2002; 40(12):4646-51. (Year: 2002).*
Hermsen CC, Telgt DS, Linders EH, van de Locht LA, Eling WM, Mensink EJ, Sauerwein RW. Detection of Plasmodium falciparum malaria parasites in vivo by real-time quantitative PCR. Mol Biochem Parasitol. Dec. 2001; 118(2):247-51. (Year: 2001).*
Kulski JK, Khinsoe C, Pryce T, Christiansen K. Use of a multiplex PCR to detect and identify *Mycobacterium avium* and M intracellulare in blood culture fluids of AIDS patients. J Clin Microbiol 1995; 33: 668-74. (Year: 1995).*
Hindiyeh, M., et al., Evaluation of a Multiplex Real-Time Reverse Transcriptase PCR Assay for Detection and Differentiation of Influenza Viruses A and B during the 2001-2002 Influenza Season in Israel, J. Clin. Microbiol. 43(2): 589-595 (2005). (Year: 2005).*
Jou NT, Yoshimori RB, Mason GR, Louie JS, Liebling MR. Single-tube, nested, reverse transcriptase PCR for detection of viable *Mycobacterium tuberculosis*. J Clin Microbiol. May 1997; 35(5):1161-5. (Year: 1997).*
Daum LT, Worthy SA, Yim KC, Nogueras M, Schuman RF, Choi YW, Fischer GW. A clinical specimen collection and transport medium for molecular diagnostic and genomic applications. Epidemiol Infect. Nov. 2011; 139(11):1764-73. Epub Dec. 16, 2010. (Year : 2011).*
Daum et al. Detection and Molecular Characterization of Clinical Influenza A and B Viruses from Original Nasal Wash Specimens Preserved in PrimeStore® MTM. The 3rd European Conference of Influenza. Sep. 13-17, 2008, Vilamoura Portugal. (Year: 2008).*
Gopinath, K., and S. Singh. 2009. Multiplex PCR assay for simultaneous detection and differentiation of *Mycobacterium tuberculosis, Mycobacterium avium* complexes and other Mycobacterial species directly from clinical specimens. Journal of applied microbiology 107(2): 425-435. (Year: 2009).*
PCT Search and Patentability Report for PCT/US2016/63767, dated Feb. 7, 2017.
Ecker, DJ, et al, "New technology for rapid molecular diagnosis of bloodstream infections," Expert Review of Molecular Diagnostics, vol. 10, No. 4, pp. 399-415, May 1, 2010; title; abstract; pp. 400, 403-407, 409-412.
Selvapandiyan, A., et al, "A novel semiquantitative florescence-based multiplex polymerase chain reaction assay for rapid simultaneous detection of bacterial and parasitic pathogens from blood," Journal of Molecular Diagnostics, vol. 7, No. 2, pp. 268-275, May 31, 2005; abstract; pp. 269-272.
Somoskovi, A, "Novel laboratory diagnostic tests for tuberculosis and their potential role in an integrated and tiered laboratory network," Tuberculosis, vol. 95, pp. 1-3, Jun. 30, 2015; abstract; pp. 2-3.
Anderson, et al, "DNA and RNA-derived assessments of fungal community composition in soil amended with sewage sludge rich in cadmium, copper and zinc," Soil Biology and Biochemistry, Pegamon, Oxford, GB, vol. 40, No. 9, Sep. 1, 2008.
Liao, J et al, "Telomerase activity in oral and maaxillofacial tumors," Oral Oncology, Elsevier Science, Oxford, GB, vol. 36, No. 4, Jul. 1, 2000.
Daum, L, et al, "A clinical specimen collection and transport medium for molecular diagnostic and genomic applications," Epidemiology and Infection, Cambridge University Press, Cambridge, GB, vol. 139, No. 11, Dec. 16, 2010.
Daum, L. et al, "A rapid, collection-to-detection PCR system of the universal detection of *Mycobacterium tuberculosis*," Jun. 29, 2011, pp. 1-1.
Papagrigorakis, M. et al, "DNA examination of ancient dental pulp incriminates typhoid fever as a probable cause of the plague of Athens," International Journal of Infectious Diseases, Hamilton, CA, vol. 10, No. 3, May 1, 2006.
Buys, et al, "Applying AFLPs in Aizoaceae: the Delosperma herbeum complex as a case study," Biochemical Systematics and Ecology, Pergamon Press, GB, vol. 36, No. 2, Dec. 13, 2007.
Thierry, et al., "Characterization of a *Mycobacterium tuberculosis* Insertion Sequence, IS6110, and Its Application in Diagnosis," Journal of Clinical Microbiology, vol. 28 No. 12, Dec. 1990, p. 2668-2673.
Austalian Exam Report for Application No. 2012239385, dated Oct. 9, 2013.
Austalian Exam Report for Application No. 2012211365, dated Oct. 9, 2013.
Max, et al Reliability of PCR-based detection of occult tumour cells: lessons from real-time RT-PCR.
EP Search Report for Application No. 13175959, dated Nov. 18, 2013.
PCT Search and Patentability Report for PCT/US2013/077038, dated Mar. 10, 2014.
CA Office Action for CA Application No. 2701168, dated Mar. 4, 2014.
PCT Search Report for PCT/US13/32354, dated May 31, 2013.
Chinese Office Action for Application No. 201080028416.4.
Chinese Search Report for Application No. 201080028416.4.
IL Exam Report for PCT/US2007/078025, dated Mar. 7, 2013.
EPO Exam Report for EP12180376, dated Feb. 8, 2013.
Canadian Office Action for application No. 2759028, dated Apr. 12, 2013.
"Development of an Internal Positive Control for Rapid Diagnosis of Avian Influenza, etc.", A.Das, et al., Journal of Clinical Microbiology, Sep. 2006, vol. 44, No. 9, pp. 3065-3073.
De Moreau de Gerbehaye, A.I. et al., "Stable Hepatitis C Virus RNA Detection by RT-PCR During Four Days Storage," BioMed Central, BMC Infectious Diseases, 2:22 (2002).
"Evaluation of PCR Testing of Ethanol-Fixed Nasal Swab Specimens, etc." A.Krafft, et al., Journal of Clinical Microbiology, Apr. 2005, vol. 43, No. 4, pp. 1768-1775.
"Abstracts—27th Annual Meeting for the European Society for Paediatric Infectious Disease, Brussels, Belgium, Jun. 9-13, 2009," The Ped. Infect. Dis. J., 28(6):e1, e75, e229 (Jun. 2009).
"AgPath-ID One-Step RT-PCR Kit," Applied Biosystems, available at http://www.abion.com/techlib/prot/bp_1005.pdf (last visited Aug. 24, 2009).
Lin, B., et al., "Broad-Spectrum Respiratory Tract Pathogen Identification Using Resequencing DNA Microarrays." Genome Res., 16:527-35 (2006).
Buck et al. BioTechniques vol. 27, pp. 528-536, Sep. 1999.
Wolff, C. et al, "Single-Tube Nested PCR With Room-Temperature-Stable Reagents," Cold Spring Harbor Laboratory Press, PCR Methods and Appl., 4:376-79 (1995).
Schultz, C.L., et al., "A Lysis, Storage, and Transportation Buffer for Long-Term, Room-Temperature Preservation of Human Clinical Lymphoid Tissue Samples Yielding High Molecular Weight Genomic DNA Suitable for Molecular Diagnosis," Am. J. Clin. Pathol., 111(6):748-52 (1999).
Characterization of Novel Influenza 2005.
"Collecting, Preserving, Shipping Specimens for the Diagnosis of Avian Influenza (H5N1) Virus Infection: Guide for Field Operations," WHO/CDS/EPR/ARO/2006.1 (2006).

(56) References Cited

OTHER PUBLICATIONS

Daum, et al., Abstract—"A Molecular Transport Medium (MTM) for Pathogen Inactivation, Ambient Transport and Preservation of RNA from Clinical Samples," ICAAC, Boston, MA, Sep. 12-15, 2010.
Daum, et al., Abstract and Poster—"Development of a Real Time Reverse-Transcription PCR (RRT-PCR) Assay for Detection of Influenze A H1N1 2009 From Clinical Resiratory Specimens," Pediatric Infectious Disease Conference ESPID, Nice, France, May 5-8, 2009.
Daum, et al., Abstract and Poster—"Development of a Real Time Reverse-Transcription PCR (RRT-PCR) Assay for Detection of Influenza A H1N1 2009 from Clinical Respiratory Specimens," Pediatric Infectious Disease Conference ESPID, Nice, France, May 5-8, 2010.
De Silva at al. Influenza A virus (A/Nonthaburi/102/2009(H1N1)) segment 4 hemagglutinin (HA) gene, partial cds. Genbank Accession No. GQ 132184.1, submitted May 9, 2009.
Spackman, E., et al., "Development of a Real-Time Reverse Transcriptase PCR Assay for Type A Influenza Vrius and the Avian H5 and H7 Hemagglutinin Subtypes," J. Clinic. Mirobiol., 40(9): 3256-60 (2002).
Hindiyeh et al. Journal of Clinical Microbiology, vol. 43, No. 2, pp. 589-595, Feb. 2005.
J. Mahoney et al., "Multiplex RT-PCR for detecting nineteen respiratory viruses," Journal of Clinical Virology, vol. 36, Jan. 1, 2006, p. S9.
"Adamantane Resistance Among Influenza, etc.", JAMA, Feb. 22, 2006, vol. 295, No. 8, pp. 891-894.
Jamie A. Blow et al., "Viral nucleic acid stabilization by RNA extraction reagent," Journal of Virological Methods, 150 (2008), Feb. 4, 2008, pp. 41-44.
"KOD Hot Start DNA Polymerase," Novagen, available at http://www.emdbiosciences.com/ProductDisplay.asp?catno=71086 (last visited Aug. 24, 2009).
Kutyavin et al. 3'-Minor groove binder-DNA probes increase sequence specificity at PCR extension temperatures. Nucleic Acid Res. (2000) vol. 28, No. 2, pp. 655-661.
"Genetic and Antigenic Analysis of the First A/New Calendonia, etc.", L.Daum, et al., Emerging Infectious Diseases, vol. 8, No. 4, Apr. 2002, pp. 408-412.
Canas, L.C., "Clinical Laboratory: Selection, Collection and Transport of Specimens for Viral Cultures." Department of the Air Force, Air Force Institute of Operational Health (AFIOH), Epidemiological Surveillance Division, SDE O1 44-5001, Virol. Proc. Man., 1-8 (2005).
Daum L.T., et al., "Molecular Analysis of Isolates From Influenza B Outbreaks in the U.S. and Nepal, 2005," Arch. of Virol., 151:1863-1874 (2006).
Daum, L.T. et al., "Real-Time RT-PCR Assays for Type and Subtype Detection of Influneza A and B Viruses," Influenza & Other Resp. Viruses 1(4): 167-75 (2007).
Daum, L.T., et al., "Abstract—Quantification of Influenza A Virus From Nasal and Lung Tissue of Cotton Rats Using Real-Time RT-PCR and Culture," 26th Annual Meeting of the European Society for Pediatric Infectious Diseases, Graz, Austria (2008).
Daum, L.T., et al., "Abstract—Development and Clinical Evaluation of Rapid Real-Time RT-PCR Assays for Detection of Influenza A and B Viruses," 26th Annual Meeting of the European Society for Pediatric Infectious Diseases, Graz, Austria (2008).
Daum, L.T., et al., "Poster—A Novel Specimen Collection Solution for Molecular Diagnostic Applications," The Pediatric Academic Societies (PAS) Annual Meeting, Honolulu, HI (2008).
Daum, L.T., et al., " Poster—A Rapid, Simplified Collection-to-Detection System for Typing and Subtyping Influenza Viruses Using Real-Time RT-PCR and Culture," American Society for Microbiology (ASM) Conference on Emerging Technologies of Medical Importance for the Diagnosis of Infectious Diseases and the Detection of Pathogenic Microbes, Beijing, China (2008).
Daum, L.T., et al., "Poster—Real-Time RT-PCR Detection of Influenza A Virus in Asymptomatic Culture-Negative Cotton Rats," The Pediatric Academic Societies (PAS) Annual Meeting, Honolulu, HI (2008).
Daum, L.T., et al., "A Rapid, Single-Step Multiplex Reverse Transcription-PCR Assay for the Detection of Human H1N1, H3N2 and B Influenza Viruses." J. of Clinic. Virol., 25(3): 345-50 (2002).
Daum, L.T., et al., "Real-Time RT-PCR Detection of Influenza Virus Within Symptomatic and Asymptomatic Family Members," The 48th Annual IDSA/ICAAC, Washington D.C. (2008).
Lowe et al. A computer program for selection of oligonucleotide primers for polymerase chain reactions. Nucleic Acids Research (1990) vol. 18, No. 7, pp. 1757-1761.
Luke T. Daum et al., "Detection and Molecular Characterization of Clinical Influenza A and B Viruses from Original Nasal Wash Specimens Preserved in PrimeStore," (2008).
Luke T. Daum et al., "Portugal Meeting Poster (Introduction, Materials, and Methods, Results, Discussion)," (2008).
"Luminex Confirms Effectiveness of xTAG Respiratory Viral Panel for Swine Flu Surveillance," Medical News Today, available at http://www.medicalnewstoday.com/printerfriendlynews.php?newsid=148498 (May 1, 2009).
"Luminex Receives FDA Clearance for an Update to the xTAG Respiratory Panel Insert Package Insert to Include Data from Two New Publications on 2009 Influenza A/H1N1," available at http://phx.corporate-ir.net/phoenix.zhtml?c=79403&p=irol-newsArticle&ID=1307416&highlight= (Jul. 14, 2009).
Borns, M. et al., "Most Accurate PCR Enzyme Inproved With Hot Start Feature," Biocompare, available at http://www.biocompare.com/technicalarticle/212/Most-Accurate-PCR-Enzyme-Improved-With-Hot-Start-Feature-from-Startagene.html (last visited Aug. 24, 2009).
Denhart, M., and Doraiswamy, V., "Master Your PCR Domain!" Promega Notes, 78: 9-12 (2001).
Master Your PCR Domain.
"Tools of Biochemistry 5A—Ways to Isolate and Purify Proteins and Other Macromolecules", Matthews, et al., Biochemistry, Second Edition, 1996, pp. 152-155.
Tortora, et al., "Tools of Biochemistry 5A—Ways to Isolate and Purify Proteins and Other Macromolecules," Microbiology—An Introduction, pp. 152-55, 4th Ed., The Benjamin/Cummings Publishing Company, Inc., United States (1992).
Matthews, et al., "Immunofluorescence and Fluorescent Antibody Techniques," Biochemistry, pp. 461-463, 2nd Ed., The Benjamin/Cummings Publishing Company, Inc., United States (1996).
Morre, et al., "RNA Amplification by Nucleic Acid Sequence-Based Amplification with an Internal Standard Enables Reliable Detection of *Chlamydia trachomatis in Cervical Scrapings and Urine Samples,*" J. of Clinical Microbiol, 34(12): 3108-3114 (1996).
http://www.ncbi.nim.nih.gov/genomes/FLU/SwineFlu2009.html. NCBI Influenza Virus Resource "CLE I. GenBank Sequence from Pandemic (H1N1) 2009 Viruses". 1237 pages.
Pheng, O.C. Et al., "Temperature Related Storage Evaluation of an RT-PCR Test Kit for the Detection of Dengue Infection in Mosquitoes," (Research Note), Tropical Biomedicine, 22(1):73-6 (2005).
"Single-Step Method of RNA Isolation by Acid Guanidinium, etc.", P. Chomczyniski, et al., Analytical Biochemistry 162, 1987, pp. 156-159.
Pamphlet—"Prime PCR System"—Longhorn Vaccines & Disagnostics.
"PCR Optimization: Reaction Conditions and Components," Applied Biosystems, Part No. 4371091, Revision C, pp. 1-6 available at http://www.appliedbiosystems.com/cms/groups/mcb_marketing/documents/generaldocuments/cms_042520.pdf (last visited Aug. 24, 2009).
"PCR-Ready Clear Supreme," Syntezza Bioscience Ltd., available at http://www.syntezza.com/egt/PCR-Ready_Clear Supreme.pdf (2006).
European Patent Office, "PCT Notification of Transmittal of the International Search Report and the Written Opinion of the International Searching Authority or the Declaration, PCT International Search Report, PCT Written Opinion of the International Searching Authority—Application No. PCT/US2007/078025," dated Nov. 13, 2008, 10 pages, Munich.

(56) References Cited

OTHER PUBLICATIONS

European Patent Office, "PCT Notification of Transmittal of the International Search Report and the Written Opinion of the International Searching Authority—Application No. PCT/US2008/078499," dated Aug. 4, 2009, 13 pages.
Ramanujam, R. et al., "Room-Temperature-Stable PCR Reagents," Cold Spring Harbor Laboratory Press, PCR Methods and Appl., 3:75-76 (1993).
Bright, R.A., et al., "Adamantane Resistance Among Influenza A Viruses Isolated Early During the 2005-2006 Influenza Season in the United States," JAMA, 295(8):891-4 (Feb. 22, 2006).
Fouchier, R.A.M. et al., "Characterization of a Novel Influenza A Virus Hemagglutinin Subtype (H16) Obtained From Black-Headed Gulls," J. of Virol. 79(5):2814-22 (Mar. 2005).
"R.A.P.I.D System," Idaho Technology Inc., available at http://www.idahotech.com/RAPID/Rapid-Water.html (last visited Aug. 24, 2009).
Magari, R.T., Assessing shelf life using real-time and accelerated stability tests, BioPharm Nov. 2003.
Rosenstraus, et al., "An Internal Control for Routine Diagnostic PCR: Design, Properties, and Effect on Clinical Performance," J. of Clinical Microbial, 36(1): 191-197 (1998).
Blacksell, S.D. et al., "The Effect of Sample Degradation and RNA Stabilization on Classical Swine Fever Virus RT-PCR and ELISA methods," J. Virol. Methods, 118(1):33-7 (2004).
"Single Tube PCR Kit Manual," Takara Bio Inc., Cat #RR021, V.02.09, pp. 1-6 available at http://www.takara-bio.us/files/manuels/TAK_RR021_TM.pdf (last visited Aug. 24, 2009).
"Taq PCR Master Mix (2x)," USB Corp., (2007).
"TechNotes Newsletter," Applied Biosystems, 14(4):1-37 (2007).
"Immunoflourescence and Fluorescent-Antibody Techniques", Tortora, et al., Microbiology—An Introduction, Fourth Edition, 1992, pp. 461-463.
"USB Taq PCR Master Mix in qPCR," USB Corporation, Tech Tips, 207 (2005).
World Health Organization, "CDC protocol of realtime RTPCR for influenza A (H1N1)," Apr. 28, 2009.
Wiecek, A., "Pocket PCR: The Whole Chain Reaction in His Hand," Biotechniques.com, Oct. 26, 2010.
Wang, Z., et al., "Identifying Influenza Viruses with Resequencing Microarrays," Emerg. Infect. Dis. 12(4):638-46 (2006).
Danila Valmori et al. "Use of human universally antigenic tetanus toxin T cell epitopes as carriers for human vaccination" Journal of Immunology Jul. 15, 1992.
PCT Search Report for PCT/US2008/074521 dated Feb. 13, 2009.
PCT Written Opinion for PCT/US2008/074521 dated Mar. 5, 2009.
PCT Search Report for PCT/US10/43546 dated Nov. 16, 2010.
PCT Search Report for PCT/US10/31716 dated Jul. 28, 2010.
PCT Written Opinion for PCT/US10/31716 dated Oct. 25, 2011.
De Folette et al. Vaccine 2006, Jun. 12, vol. 24, No. 44-46, pp. 6597-6601.
Galarza et al. Viral Immunity 2005, vol. 18, No. 2, pp. 365-372.
Arend et al. Infection and Immunity, 2000, vol. 68, No. 6, pp. 3314-3321.
Geysen, et al., "Use of Peptide Synthesis to Probe Viral Antigens for Epitopes to a Resolution of a Single Amino Acid," Proc. Natl. Acad. Sci., 81, pp. 3998-4002 (1984).
Tolman, et al., "Cyclic V3-Loop Related HIV-1 Conjugate Vaccines," Int. J. Peptide Protein Res., 41, pp. 455-466 (1993).
Conley, et al., "Immunogenicity of Synthetic HIV-1 Gp120 V3-Loop Peptide-Conjugate Immunogens," Vaccine, 12(5), pp. 445-451 (1994).
Schneider, et al., "Induction of CD8+T Cells Using Heterologous Prime-Boost Immunisation Strategies," Immunol. Rev., 170, pp. 29-38 (1999).
Tanghe, et al., "Improved Immunogenicity and Protective Efficacy of a Tuberculosis DNA Vaccine Encoding Ag85 by Protein Boosting," Infect. and Immun., 69(5), pp. 3041-3047 (2001).
Gonzalo, et al., "A Heterologous Prime-Boost Regime Using DNA and Recombinant Vaccinia Virus Expressing the Leishmania infantum P36/LACK Antigen Protects BALB/c Mice from Cutaneous Leishmaniasis," Vaccine, 20, pp. 1226-1231 (2002).

Meyer, et al., "Complement-Mediated Enhancement of Antibody Function for Neutralization of Pseudotype Virus Containing Hepatitis C Virus E2 Chimeric Glycoprotein," J. of Virol., 76(5) pp. 2150-2158 (2002).
Robinson, "New Hope for an AIDS Vaccine," Nat. Rev. Immunol., 2, pp. 239-250 (Apr. 2002).
Lu, et al., "Multiepitope Trojan Antigen Peptide Vaccines for the Induction of Antitumor CTL and Th Immune Responses," J. of Immunol., 172, pp. 4575-4582 (2004).
Westerfield, et al., "Peptides Delivered by Immunostimulating Reconsituted Influenza Virosomes," J. of Peptide Sci., 11(11), pp. 707-712 (2005).
Gerhard, et al., "Prospects for Universal Influenza Virus," Emerging Infectious Diseases, 12(4), pp. 569-574 (Apr. 2006).
Luo, "Structural Biology: Antiviral Drugs Fit for a Purpose," Nature, 443, pp. 37-38 (Sep. 1, 2006).
PepTcell Ltd., "Technology," http://www.peptcell.com/technology.aspx (2007).
Stoloff, et al., "Synthetic Multi-Epitope Peptides Idenitifed in Silico Induce Protective Immunity Against Multiple Influeza Serotypes," Eur. J. of Immunol., 37(9), pp. 2441-2449 (Aug. 2, 2007).
Depla, et al., "Rational Design of a Multiepitope Vaccine Encoding T-Lymphocyte Epitopes for Treatment of Chronic Hepatitis B Virus Infections," J. of Virol., 82(1), pp. 435-450 (Jan. 2008).
Chien et al. J. Clin. Microbiol. 1999, vol. 37, No. 5, 1393-1397.
Ishioka et al. J. Immunol. vol. 162, pp. 3915-3925.
Lederman et al. Molecular Immunology 1991, vol. 28, No. 11, pp. 1171-1181.
PCT Search Report for PCT/US2007/078025 dated Oct. 28, 2008.
PCT Written Opinion for PCT/US2007/078025 dated Mar. 17, 2009.
PCT Search Report for PCT/US2008/078499 dated Jul. 23, 2009.
CA Office Action for PCT/US2007/078025, dated Jan. 4, 2011.
EPO Exam Report for PCT/US2007/078025, dated Dec. 30, 2011.
EPO Exam Report for PCT/US2007/078025, dated Aug. 26, 2010.
EPO Exam Report for PCT/US2007/078025, dated Jul. 6, 2009.
EPO Exam Report for PCT/US2007/078025, dated May 18, 2009.
AU Exam Report for PCT/US2007/078025, dated Nov. 19, 2010.
IL Exam Report for PCT/US2007/078025, dated Mar. 16, 2011.
NZ Exam Report for PCT/US2007/078025, dated Jul. 7, 2010.
Israel Office Action dated Jul. 19, 2012.
EPO Supplementary Search Report for PCT/US10/31761, dated Jul. 13, 2012.
CA Office Action for PCT/US2008/078499, dated Mar. 29, 2012.
PCT Written Opinion for PCT/US2008/078499, dated Jul. 4, 2010.
"Monolithic Silica Extraction Tips for Sample Preparation," CP-Analytica, available at http://cp-analytica (last visited Oct. 25, 2010).
Barnard, et al., "Suitability of new chlamydia transport medium for transport of herpes simplex virus," J. of Clin. Microbiol., 24(5): 692-695 (1986).
Eroglu, et al., "Successful cyropreservation of mouse oocytes by using low concentrations of trehalose and dimethylsylfoxide," Biol. of Rep. 80:70-78 (2009).
Gelmi, et al., "Bacertial survival in different transport media," European Congress of Clinical Microbiology and Infectious Diseases (ECCMID), May 28-31, 2000 (poster).
Higashiyama, T., "Novel functions and applications of terhalose," Pure Appl. Chem. 74(7): 1263-1269.
H1N1 RTPCR Primer/Probe Sets, Intergrated DNA Technologies—H1N1, available at http://www.idtdna.com/catalog/h1n1/page1.aspx.
Johnson, F.B., "Transport of viral specimens," Clin. Microbiol. Rev. 3(2): 120-131 (1990).
Sponseller, et al., "Influenza A pandemic (H1N1) 2009 virus infection in domestic cat," Emerg. Infect. Dis. (e-publication) (2010).
PCT Patentability Report for PCT/US2010/043546, dated Jan. 31, 2012.
PCT Search Report and Patentability Report for PCT/US2008/074521, dated Mar. 2, 2010.
Miyazaki, et al., "Development of a monolithic silica extraction top for the analysis of proteins," J. Chromatogr. A., 1043(1): 19-25 (2004) [abstract only].

(56) References Cited

OTHER PUBLICATIONS

PCT Patentability Report for PCT/US2012/35253, dated Sep. 21, 2012.
Taiwan Office Action dated Aug. 20, 2012.
Henke et al., Nucleic Acids Research 25(19): 3957-3958 (1997).
Yue et al., Diagnostic Microbiology and Infectious Disease, 48(1): 47-54 (2004).
Canadian Office Action for application No. 2697373, dated Feb. 19, 2013.
EP Search Report for Application No. 15184002.2.
EP Opinion for Application No. EP15184002, dated Mar. 11, 2016.

\* cited by examiner

COMPOSITIONS AND METHODS FOR DETECTING AND QUANTIFYING NUCLEIC ACID SEQUENCES IN BLOOD SAMPLES

REFERENCE TO RELATED APPLICATIONS

This application is a continuation-in-part of U.S. application Ser. No. 14/048,875 filed Oct. 8, 2013, which is a continuation-in-part of U.S. application Ser. No. 13/094,809 filed Apr. 26, 2011, which issued as U.S. Pat. No. 8,652,782 on Feb. 18, 2014, which is a continuation-in-part of U.S. application Ser. No. 12/916,263 filed Oct. 29, 2010; a continuation-in-part of U.S. application Ser. No. 12/510,968 filed Jul. 28, 2009, which issued as U.S. Pat. No. 8,097,419 on Jan. 17, 2012; a continuation-in-part of U.S. application Ser. No. 12/426,890 filed Apr. 20, 2009, which issued as U.S. Pat. No. 8,080,645 on Dec. 20, 2011, and a continuation-in-part of U.S. application Ser. No. 12/243,949 filed Oct. 1, 2008, which issued as U.S. Pat. No. 8,084,443 on Dec. 27, 2011, and claims priority to U.S. Provisional Application No. 60/976,728 filed Oct. 1, 2007;

a continuation-in-part of U.S. application Ser. No. 14/527,281 filed Oct. 29, 2014, which claims priority to U.S. Provisional Application No. 61/897,015 filed Oct. 29, 2013; which is a continuation-in-part of U.S. application Ser. No. 13/890,512, filed May 9, 2013, which issued as U.S. Pat. No. 9,365,904 on Jun. 14, 2016, and claims priority to U.S. Provisional Application No. 61/737,250 filed Dec. 14, 2012, U.S. Provisional Application No. 61/695,960 filed Aug. 31, 2012, U.S. Provisional Application No. 61/646,060 filed May 11, 2012, and U.S. Provisional Application No. 61/644,876 filed May 9, 2012;

a continuation-in-part of International Application No. PCT/US2015/32432 filed May 26, 2015, which claims priority to U.S. Provisional Application No. 62/003,976 filed May 28, 2014; and claims priority to U.S. Provisional Application No. 62/260,064 filed Nov. 25, 2015, and each of these applications are incorporated in their entirety.

FIELD OF THE INVENTION

The present invention is directed to compositions and methods for quantitating nucleic acid sequences within a biological sample, such as obtained from a blood sample, and also for the assessment of infection over time by determining genomic and mRNA ratios of multiple samples. In particular, the compositions and methods of the invention allow for the rapid detection and identification of infections in MTB sepsis.

BACKGROUND OF THE INVENTION

Mycobacteria are unicellular, aerobic, Gram-positive bacteria. Typically, mycobacteria have a thick hydrophobic cell wall and lack an outer cell membrane. Infections caused by mycobacteria can be active within a host, or latent and asymptomatic. The emergence of multidrug resistant strains, the need for prolonged antibacterial therapy, and poor patient compliance, has made treatment of mycobacterial infections difficult, particularly in developing nations. The emergence of multidrug resistant (MDR) strains of *M. tuberculosis*, in particular, has made diagnosis and treatment of TB a high priority in developing African populations.

Mycobacteria are typically classified as acid-fast Gram-positive bacteria due to their lack of an outer cell membrane. Acid-fast staining methods that are frequently used are the Ziehl-Neelsen stain or the Kinyoun method. They do not, generally, retain the crystal violet stain well and so are not considered a typical representative of Gram-positive bacteria. They do, however, contain a unique cell wall structure, which is thicker than that present in most other bacterial species. Typically, rod shaped, the cell wall consists of a hydrophobic mycolate layer (containing mycolic acids) and a peptidoglycan layer which is held together by arabinogalactan, a polysaccharide. This cell wall structure aids the mycobacteria in their ability to survive drastic environmental changes and contributes to the hardiness of the *Mycobacterium* species, as well in the difficulty in treating tuberculosis and leprosy patients, both of which are caused by different *Mycobacterium* species. Mycolic acids are strong hydrophobic molecules that form a lipid shell around the organism and affect permeability properties at the cell surface. Mycolic acids are thought to be a significant determinant of virulence in some *Mycobacterium* species. Most likely, they prevent attack of the mycobacteria by cationic proteins, lysozyme, and oxygen radicals in the phagocytic granule. They also protect extracellular mycobacteria from complement deposition in serum.

Additionally, mycobacteria are typically slow growing organisms, contributing to the difficulty of culturing the species. Due to their unique cell wall, they can survive long exposure to acids, alkalis, detergents, oxidative bursts, lysis by complement, and many antibiotics. Most mycobacteria are susceptible to the antibiotics clarithromycin and rifamycin, but antibiotic-resistant strains have emerged.

Members of the *Mycobacterium tuberculosis* complex, i.e., *M. tuberculosis, M. bovis, M. africanum, M. microti, M. cannetti, M. caprae* and *M. pinnipedi*, the causative agents of tuberculosis, have all of the above stated characteristics of mycobacteria. The primary consequence of mycobacterial infection (and particularly, infection by one or more species of *Mycobacterium* genus) in humans is tuberculosis (TB), a contagious infection caused by members of the "*M. tuberculosis* complex," which include, e.g., pathogenic strains of the species *M. tuberculosis, M. bovis, M. africanum, M. microti, M. cannetti, M. caprae* and *M. pinnipedi*. TB typically attacks the lungs in mammalian hosts, but can also spread to other organs and regions of the body including, for example, bone, joints, kidneys, and the abdomen, etc. Members of the *M. tuberculosis* complex are closely related genetically, and possess highly-conserved 16S rRNA sequences across the genus.

TB can be acquired by breathing in air droplets from a cough or sneeze of an infected person. Accordingly, collection of biological samples suspected of containing members of the *M. tuberculosis* complex involves the collection of sputum from patients suspected of being infected with the same. Sputum is coughed up expectorate from the airways and ideally contains little to no saliva or nasal secretion, so as to avoid contamination of the sputum sample with oral bacteria. Sputum mainly contains mucus, a viscous colloid which is rich in glycoproteins. Patients suspected of having tuberculosis typically have an increased mucus viscosity, as well as increased production of mucus. In addition to mucus, sputum may contain blood, i.e., hemoptysis may occur, and/or pus, i.e., be purulent in nature. Symptoms of an active tubercular infection can include chronic cough (typically with blood-tinged sputum), fever, nocturnal hyperhidrosis, chronic fatigue, pallor, weight loss, and cachectic wasting ("consumption"). Other symptoms can include breathing difficulties, thoracic pain and wheezing ("Pulmonary Tuberculosis," PubMed Health). If an inhaled tubercle *Bacillus* settles in a lung alveolus, infection occurs, followed by alveolocapillary dilation, and endothelial cell swelling. Alveolitis results with intracellular replication of the tubercle bacilli and an influx of polymorphonuclear leukocytes to the alveoli. The organisms then spread through the lymph system to the circulatory system, and then throughout the body. In HIV patients, MTB and other pathogens can enter the blood stream and be indicative of a tissue, or organ infection, or the patient may have septicemia and shock and have a rapidly fatal infection. (Jacob, et al)

Although *M. tuberculosis* infects less than 200000 people annually in the United States, according to the World Health Organization (WHO) nearly two billion people worldwide may be infected, 90% of whom can remain asymptomatic for years following infection. Left untreated, TB is fatal in >50% of the infected population, and in disseminated forms of the disease, the mortality rate approaches 90%.

Because of the chronic and debilitating persistence of TB infection, co-infection with one or more secondary pathogens, including in particular, human immunodeficiency virus (HIV), is also widespread. In 2007, there were at least 1.37 million cases of HIV-positive TB, concentrated primarily in emerging populations where diagnosis and treatment are often limited, ineffective, and/or cost-prohibitive.

Conventional diagnosis of a TB infection typically relies on a combination of physical examination (e.g., chronic persistent cough, enlarged or tender lymph nodes, pleural effusion, unusual breath sounds, and, in later stages of the disease, characteristic "clubbing" of the fingers or toes) and diagnostic testing (e.g., sputum examination, microbial culture and nucleic acid testing of specimens, bronchoscopy, CT scan or X-ray of the chest, pulmonary biopsy, thoracentesis, interferon-γ (gamma) blood test, and tuberculin skin test).

The "standard" of TB diagnostics, culturing of mycobacterial organisms, is difficult, due in part to their long generation times, i.e., twenty-four hours for *M. tuberculosis*. In addition, mycobacteria are typically present at low levels in many specimens from infected individuals. Culturing from a clinical specimen can take anywhere between four to eight weeks, during which time a patient may become seriously ill and contagious to others. In addition, MTB culturing requires the collection, transport and maintenance of viable mycobacterial organisms in a sample until such time as the sample can be analyzed in a lab setting. In countries where TB is prevalent, and health care is minimal, this may not be an option, thus increasing the risk of spreading infection.

The majority of clinical diagnostic laboratories employed traditional culture for pathogen identification that typically requires 3-7 days for most viruses and longer for some bacteria, including up to about 21 days for the culturing of MTB. Traditional culture requires specimen collection of viable microbes, frozen transport, and propagation and handling of potentially infectious and often unknown biological microbes. Furthermore, many infectious agents, e.g., highly pathogenic avian influenza, SARS, *M. tuberculosis* complex, etc., are BSL-3 level pathogens that require specialized facilities and precautions for analysis. There are challenges in obtaining, shipping and maintaining high-quality, viable biological specimens for culture. Specimens must be shipped using a cold chain, most often dry ice. Transporting potentially infectious samples from remote sites or across international borders using commercial transit can be costly and tedious, particularly when specimens must be received frozen.

Collection is the first step in diagnostic platforms or molecular protocols requiring the detection of potentially minute amounts of nucleic acids from microbes. Regardless of the nucleic acid test used or the RNA/DNA extraction protocol, specimen collection, specifically the inactivation of potentially infectious agents and the preservation and stability of pathogen RNA/DNA remains a critical gap in clinical diagnostics, especially for use around the world.

Typically, patients suspected of having tuberculosis are asked to cough hard and then expectorate into a specimen cup in order to obtain a sputum sample. Usually, this procedure is done in a well ventilated area so as to minimize the potential for spreading infective mycobacteria. Patients may be asked to repeat this procedure in order to collect enough sputum for analysis, typically in amounts from about 5 mL to about 20 mL. Typically, collected sputum samples are refrigerated until further analytic procedures, such as cell culturing or decontamination procedures to inactivate or kill any microorganisms contained within the sample, can be performed. In order to detect *Mycobacterium tuberculosis* in a sputum sample, an excess of 10,000 organisms per mL of sputum are needed to visualize the bacilli with a 100× microscope objective (1000× magnification). Direct smear microscopy of sputum samples from tuberculosis patients is typically regarded as an effective tool for monitoring patient response to treatment. Typically, more acid fast bacilli will be found in the purulent portions of the sputum.

The field of clinical molecular diagnostics changed drastically with the advent of polymerase chain reaction (PCR), and subsequently, real-time PCR. Real-time (RT-PCR) and real-time reverse transcription PCR (rRT-PCR) can deliver superior sensitivity and specificity results in hours. Thus, the majority of current diagnostic laboratories have transitioned from traditional culture to nucleic acid testing (NAT) such as real-time PCR. While PCR viral loads for HIV have been done for years, MTB, malaria, influenza and other organisms have not been quantified from the blood for determining infection severity or to monitor the course of disease or effect of treatment.

Nucleic acid amplification testing for TB includes the use of standard polymerase chain reaction (PCR) techniques to detect mycobacterial DNA in patient sputum specimens, nucleic acid probes to identify mycobacteria in culture, restriction fragment length polymorphism (RFLP) analysis to compare different strains of TB for epidemiological studies, and genetic-based susceptibility testing to identify drug-resistant strains of mycobacteria. The complete genome of *M. tuberculosis* has been sequenced and published; currently two nucleic acid amplification-based tests for TB have been approved for use in the United States by the Food and Drug Administration (FDA), The first, known as the "Enhanced Amplified *Mycobacterium Tuberculosis* Direct Test" (E-MTD, Gen-Probe, San Diego, Calif., USA), is approved for detection of *M. tuberculosis* complex bacteria in acid-fast bacilli in both smear-positive and smear-negative respiratory specimens from patients suspected of having TB. The E-MTD test combines isothermal transcription-mediated amplification of a portion of the 16S rRNA with a detection method that uses a hybridization probe specific for *M. tuberculosis* complex bacteria. The second, known as the AMPLICOR® *Mycobacterium tuberculosis* Test (AMPLICOR®, Roche Diagnostics, Basel, Switzerland), has been approved for the detection of *M. tuberculosis* complex bacteria only in smear-positive respiratory specimens from patients suspected of having TB. This test uses PCR to amplify a portion of the 16S rRNA gene that contains a sequence that hybridizes with an oligonucleotide probe specific for *M. tuberculosis* complex bacteria. ("Report of an Expert Consultation on the Uses of Nucleic Acid Amplification Tests for the Diagnosis of Tuberculosis," Centers for Disease Control and Prevention).

Results have indicated that the sensitivity and specificity of these tests tends to vary depending on geographical location and risk factors. In addition, these techniques are for detecting MTB in sputum, not blood and require complex laboratory conditions and equipment to be performed, thus reducing the speed and sensitivity of the test. For these and other reasons, there remains a need in the art for reliable and accurate methods for detection of bacterial pathogens (and other microbes) in blood samples, and in particular, methods for rapidly identifying and quantifying such pathogens in field applications, remote locations, and in developing countries where conventional laboratories are lacking, and financial resources are limited. In particular, compositions for the safe collection, handling, and transport of pathogenic specimens, as well as molecular biology-based methods for the rapid blood bacterial load quantification directly from whole blood specimens collected and transported in PrimeStore®.

SUMMARY OF THE INVENTION

The present invention overcomes the problems and disadvantages associated with current strategies and designs, and provides new composition, tools and methods for quantifying the bacterial load in the blood and severity of disease state.

On embodiment of the invention is directed to methods of quantifying microorganisms in a blood sample comprising: combining the blood sample with a collection composition to form a mixture, wherein the composition comprises a chelating agent, a chaotrope, a detergent, a reducing agent, a chelator and a buffer together present in an amount sufficient to denature proteins, inactivate nucleases, and kill pathogens, and does not interfere with a PCR; combining at least a portion of the mixture with a PCR-ready composition to form a reaction mixture containing microorganism-specific sequences, wherein the PCR-ready composition comprises a heat-stable polymerase; a mix of deoxynucleotide tri phosphates; a pair of PCR primers configured to amplify by PCR a nucleic acid sequence that is specific for the microorganisms; a chelating agent; an osmolarity agent; an albumin; at least two salts at least one of which is a magnesium salt; and a buffer present at a pH of about 6.5 to about 9.0, wherein the pKa of the composition is within about one unit of the pH at a selected temperature, wherein the components are combined with nuclease-free water; PCR amplifying the microorganism-specific sequences of the reaction mixture to form amplification products; and quantitating the amplification products to determine the quantity of microorganisms present in the blood sample. Preferably the heat-stable polymerase is a Taq polymerase, a high fidelity polymerase, a Pfu polymerase, a hot start polymerase, or a next gen polymerase. The collection composition may further comprise a dye such as, for example, fluorescein, 5-carboxy-X-rhodamine or ROX. Preferably the pH of the collection composition is from about 6.5 to about 7.5 and the pKa is within 0.5 of the pH of the buffer at ambient temperature. More preferably the pKa of the collection composition is within 0.2 of the pH of the buffer at ambient temperature, wherein the PCR-ready composition has a pH from about 6.5 to 7.0. Preferably the pair of PCR primers are each from about 18 to 35 nucleotides in length. Also preferably, the microorganisms are bacteria, virus, fungi, parasites or combinations thereof. Preferably the bacteria are MTB, the virus is HIV, or the parasites is a *Plasmodium* species and/or *Plasmodium falciparum*. Also preferably, the composition comprises a control nucleic acid present in the PCR-ready composition at a concentration of about 1 fg to about 1 ng and PCR amplification of the control sequence provides a quantitative measure of the PCR amplification of the microorganism-specific sequences. Preferred are high throughput apparatus and methods for rapidly quantitating amplification products to determine the quantity of microorganisms present in multiple blood samples comprising repeated cycles of the methods of the invention.

Another embodiment of the invention is directed to methods for quantifying multiple different microorganisms in a biological sample comprising: contacting the biological sample with a collection composition to form a mixture containing sequences that are specific to each different microorganism; combining at least a portion of the mixture with a PCR-ready composition to form a reaction mixture; performing PCR on the reaction mixture to form amplification products that are specific for each of the different microorganisms; detecting the quantity of each amplification product; and determining the quantity of each microorganism in the sample. Preferably each amplification product is compared with a control nucleic acid to determine the quantity of each microorganism in the sample. Also preferably the quantity of each amplification product provides a measure of the severity of infection attributable to each of said different microorganisms. Preferably, the quantity of each amplification product provides a measure of the level of infection attributable to each of said different microorganisms and/or a measure of the disease state of the individual attributable to each of said different microorganisms. Preferred embodiments are high throughput apparatus and methods for rapidly determining the quantity of each microorganism in the sample comprising repeated cycles of the method of the invention.

Another embodiment of the invention is directed to method of tracking the progression of an infectious disease of an individual wherein the infectious disease is attributable to a microorganism comprising: obtaining multiple blood samples from the individual over a period of time; contacting each blood sample with a collection composition to form a mixture containing sequences that are specific to the microorganism; combining at least a portion of the mixture with a PCR-ready composition to form a reaction mixture; performing PCR on the reaction mixture to form amplification products that are specific for the microorganism; detecting the quantity of microorganisms present in each sample; and determining the progression of the infection disease of the individual. Preferably the individual has multiple infections attributable to multiple microorganisms and tracking the progression of each infectious disease. Preferably the multiple infections include at least two of MTB, *Plasmodium* and HIV. Preferred are high throughput apparatus and methods for rapidly determining the severity, progression or resolution of the infectious disease of the individual comprising repeated cycles of the method of the invention.

Another embodiment of the invention is directed to kits comprising the collection and PCR-Ready compositions, each contained within a sterile vessel configured for addition of a biological sample and thermal cycling, and instructions for determining the presence or absence of a pathogen from the results of the thermal cycling.

Another embodiment of the invention is directed to methods for rapidly determining the development of an infection of an individual comprising: contacting each of multiple biological samples collected from the individual suspected of containing an infectious microorganism over multiple periods of time with a collection composition to form multiple reaction mixtures, wherein each reaction mixture represents one of the multiple periods of time; separately combining a portion of each reaction mixture with a PCR-ready composition containing at least a reverse transcriptase to convert mRNA sequences of the infectious microorganism to DNA sequences; performing a PCR on each reaction mixture to produce amplification products of the DNA sequences of the infectious microorganism and amplification products of a genomic sequence of the infectious microorganism; detecting the quantity and/or ratio of the amplification products of the DNA sequences and the amplification products of the genomic sequence in each reaction mixture; and determining a ratio of amplification products from the DNA sequences and amplification products from genomic sequences to determine the development of the infection. Preferably the infection is bacterial, viral, fungal, parasitic, or a combination thereof. Bacterial infections that can be determined according to the invention include Mycobacteria tuberculosis, viral infections that can be determined according to the invention include influenza virus, HIV or Zika virus, and parasitic infections that can be detected according to the invention include *Plasmodium falciparum*. Preferably the multiple biological samples comprise blood, serum, sputum, saliva, nasal discharge, biopsied material, or skin scraping, and the multiple periods of time comprise hours, days or weeks. Preferably when the invention shows a decrease in the quantity or ratio of amplification products of the DNA sequences as compared to the amplification products of the genomic sequences over time indicates a reduction of the development of the infection and an increase in the quantity or ratio of amplification products of the DNA sequences as compared to the amplification products of the genomic sequences over time indicates an increase of the development of the infection. The methods of the invention further comprise administering a pharmaceutical agent to the individual to assess effectiveness. Preferably the pharmaceutical agent is an antibody, a drug, an antibiotic, a natural product, a manufactured product, an antimicrobial agent, a placebo or a combination thereof.

Other embodiments and advantages of the invention are set forth in part in the description, which follows, and in part, may be obvious from this description, or may be learned from the practice of the invention.

DESCRIPTION OF THE FIGURES

FIG. 2A Electrophoresis gel of Sample 1 of RT-PCR of MTB 85a.

FIG. 2B Electrophoresis gel of Sample 2 of RT-PCR of MTB 85a.

DESCRIPTION OF THE INVENTION

Figure 1:
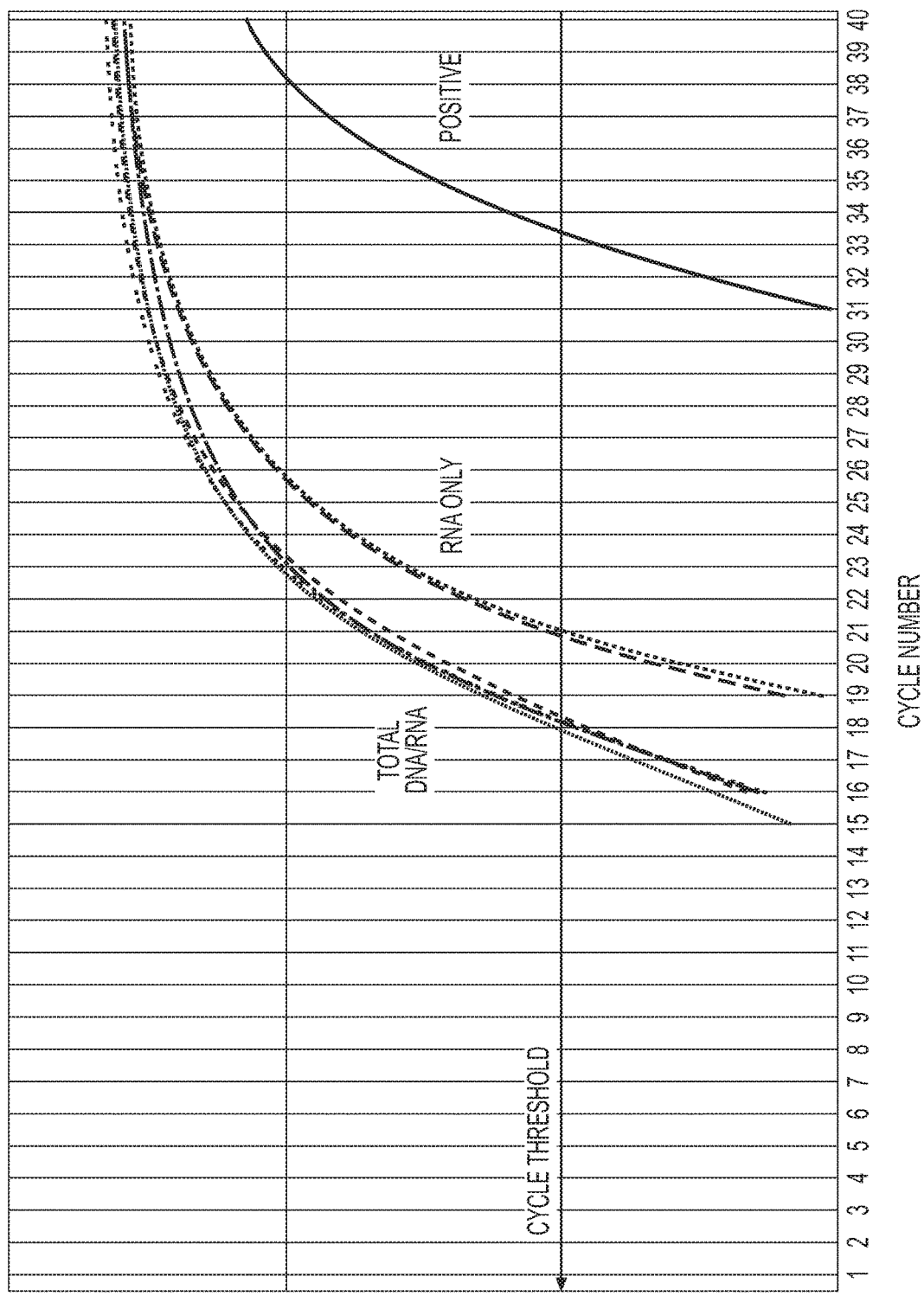
FIG. 1 MTB PrimeMix® HSP (heat-shock protein) Real-time RT-PCR Assay for detection of total nucleic acid and RNA (qPCR ABI 7500 cycle threshold ($C_T$) values).

The present invention overcomes these and other inherent limitations in the prior art by providing useful, non-obvious, and novel compositions and methods to safely collect, handle and transport biological samples suspected of containing pathogenic organisms, as well as methods for rapidly detecting, identifying, quantitating and tracking those pathogens and the severity of infections through molecular biology-based nucleic acid testing. In particular, methods are provided for specifically quantifying one or more strains of pathogenic microorganisms such as bacteria, viruses, fungus and parasites. In particular applications, the invention encompasses a product that permits the collection of a blood specimen, preparation of the target specimen for assaying, isolation of genomic material from the specimen, and subsequent processing of the genomic material to quantity one or more organisms, if present, in the biological sample. When coupled with one or more specimen collection devices, the compositions disclosed herein permit safe, collection, transport and storage of biological specimens, even for those collected in remote or "field" applications, wherein the time from sample collection to sample assay may be hours to days, or even weeks.

The invention further encompasses compositions and methods that simplify and expedite specimen collection, preparation and molecular quantitation of microorganisms, specifically bacteria that are the causative agents of sepsis, bacteremia, viremia and infections and diseases such as tuberculosis (*Mycobacterium tuberculosis*), malaria (*Plasmodium falciparum*), HIV and other disorders (e.g., genetic diseases and disorders). In particularly preferred applications, the invention encompasses a product whereby the blood specimen is collected, transported and rapidly prepared for downstream PCR and quantification without the need for a cold chain or costly and time-consuming sample decontamination and specimen emulsification. One type of molecular quantitation product includes a thermo-stabile, all-inclusive PCR mixture of primers, probes and enzymes in a ready-to-use solution or suspension. This product can be used in central labs and with high through-put systems or in rural or mobile clinics with minimal capabilities and in the absence of reliable community electric power, or even with a hand-held device. The invention also encompasses a method for epidemiologic and outbreak surveillance, pandemic and epidemic tracking, monitoring of individual patient severity and/or recovery including recovery from treatment, and microbial sequencing directly from field samples at the site of collection or by using inexpensive, simplified, safe shipping through standard mail at ambient temperature. This invention also encompasses a molecular quantitation kit for safe site of care collection, rapid extraction and rapid PCR quantitation of microbes, specifically pathogens.

Preferably the population of polynucleotides so obtained from the method are stable, such that the nucleic acids do not substantially degrade, and the integrity of the obtained population of polynucleotides will preferably be at least substantially maintained, so that the obtained polynucleotides are substantially intact, and present in the blood sample in the form that they were in when the cells containing them were initially liberated/lysed by the action of the components present in the composition. As noted herein, in preferred applications of the invention, the population of pathogen-specific polynucleotides obtained using the disclosed methods are substantially stable and non-degraded such that they can be maintained for significant periods of time even at less-than-ideal ambient temperatures (e.g., at a temperature of about 0° C. to even about 40° C. or more) for extended periods of time (e.g., for periods of several hours to several days to several week or months even) without significantly degrading the liberated nucleic acids, thereby making them suitable for downstream molecular analysis (e.g., template-dependent amplification reactions et al.) days to weeks after extraction of the nucleic acids takes place, even when it is not possible to store the populations of polynucleotides extracted from the samples frozen, on ice, or refrigerated between initial sample collection and subsequent molecular analysis.

Preferably the blood samples will be of biological, clinical or veterinary origin, and in certain embodiments, the samples are preferably of human origin, and in particular, from humans that have, are suspected of having, or are at risk for developing a microbial infection, such as an infection caused by MTB or one or more strains or species of the genus *Mycobacterium*. The individuals from which the samples are taken may be patients that also have, are suspected of having, or are at risk for developing one or more secondary or tertiary medical conditions, and in particular bacterial sepsis. An advantage of the methods of the invention for sepsis includes the aspect that the presence and degree of infection can be determined quickly and thereafter treatment begun before the patient succumbs as would otherwise occur with conventional methods for detection of MTB that require incubation and therefore days to weeks to determine the presence of an active infection. According to the methods of the invention, no incubation of the sample is necessary before the methods of the invention can be performed. The compositions and methods of the invention are preferably applied to the rapid detection of Mycobacteria in septic patients. Preferably the rapid detection is within one week, more preferably within five days, more preferably within four days, more preferably within three days, more preferably within two days, more preferably within one day, and more preferably within 12-24 hours of the collection of patient samples which are preferably blood samples. Accordingly, only with the compositions and methods of the invention can the patient be properly assessed and treatment begun in a reasonable time to allow for the possibility of a cure.

Preferably the population of nucleic acid segments contained with the plurality of isolated and purified polynucleotides obtained from a sample will be suitable for primer-dependent amplification, and particularly so, when the polynucleotides are stored in the composition for a period of about 1 to about 90 days between the time of sample collection and molecular analysis, even when stored at less-than-ideal storage conditions, including, for example, storage under ambient temperature of about 0° C. to about 40° C., preferably at ambient temperatures.

The methods of the invention may further include the step of quantifying within the obtained population of pathogen-specific polynucleotides the presence of at least a first and preferably multiple pathogen-specific nucleic acid segments by contacting the population with labeled oligonucleotide detection probes. Preferably there are at least two probes wherein the levels of labeled hybridization products are indicative of the quantity of pathogen-specific nucleic acid segments in the obtained population of polynucleotides. Also preferably the pathogen-specific probes are individually detected and quantitated for determining the state of infection of each pathogen. The state of infection can be determinative of the degree of severity of the infection (including distinguishing between dormant infections and asymptomatic infectious carriers), the risk of transmission, the effectiveness or ineffectiveness of a treatment and the tracking of any of these conditions over periods of time.

The method may also preferably further include at least the steps of (a) performing at least one thermal cycling step, wherein the cycling comprises at least a first amplifying step and at least a first hybridizing step, wherein the at least a first amplifying step comprises contacting the obtained population of polynucleotides with a composition that comprises at least a pair of distinct, independently-selected, specific amplification primers, a thermostable polymerase, a first osmolarity agent comprising betaine or another cationic functionalized zwitterionic compound, at least a first reference dye, and a plurality of deoxynucleoside triphosphates to produce at least a first pathogen-specific amplification product; and (b) quantifying the presence of the amplification product so produced by contacting it with a first labeled pathogen-specific oligonucleotide detection probe, wherein the presence of a labeled hybridization product is indicative of the level of one or more pathogen-specific nucleic acid segments in the obtained population of polynucleotides.

The methods may further include the step of performing a primer-dependent amplification of at least a first sequence region of the internal positive control nucleic acid segment in the obtained population of polynucleotides, and quantitating the amount of the internal positive control nucleic acid segment present in the obtained population of polynucleotides.

Likewise, the method may further optionally include the step of comparing the amount of the internal positive control nucleic acid segment present in the composition at one or more steps along the analytical process, to the amount of IPC that was present in the original composition before the sample was initially added to the lysis/storage/transport medium, or to the amount of target nucleic acids that were present in the original composition. Such comparison may serve to demonstrate that the amount of IPC still contained in the sample in a downstream point of assay is comparable to, or substantially the same as, the known amount of IPC that was present in the collection composition before the sample was added to it, and may serve to quantitate the amount of target nucleic acids of interest in the collected samples, or downstream assayed components. Such information may also be indicative of the amount of the nucleic acids remaining in the sample as compared to what was originally present, and may provide an estimate of the degree of sample degradation of the polynucleotides originally present over time. In certain preferred embodiment primer-dependent amplification of the least a first sequence region of the internal positive control nucleic acid segment is performed subsequent to the amplification of the pathogen-specific nucleic acid segment, while in other aspects, the primer-dependent amplification of the least a first sequence region of the internal positive control nucleic acid segment is performed substantially simultaneously with the amplification of the pathogen-specific nucleic acid segment.

Samples are preferably sample of blood obtained from a mammal (e.g., humans, non-human primates, pets, domesticated livestock). Samples may be obtained at any suitable time or multiple samples obtained repeatedly over a period of time such as, for example, over a period of hours, days, weeks, months or longer. By obtaining and testing samples over a period of time, the disease or infection can be tracked and the state of infection or disease determined at multiple times. In addition, tracking an infection allows for assessing the usefulness or viability of a drug, pharmaceutical product, or treatment against the disease whose progression is being tracked.

Microorganisms and infections that can be quantitated with the methods of the invention include, without limitation, prokaryotes such as the archaebacteria and eubacteria; cyanobacteria; fungi, yeasts, molds, actinomycetes; spirochetes, and mycoplasmas, e.g., MTB); viruses (including, without limitation the Orthohepadnaviruses [including, e.g., hepatitis A, B, and C viruses], human papillomavirus, human immunodeficiency virus (HIV), Flaviviruses [including, e.g., Dengue virus], Lyssaviruses [including, e.g., rabies virus], Morbilliviruses [including, e.g., measles virus], Simplexviruses [including, e.g., herpes simplex virus], Polyomaviruses, Rubulaviruses [including, e.g., mumps virus], Rubiviruses [including, e.g., rubella virus], Varicellovirus [including, e.g., chickenpox virus], rotavirus, coronavirus, cytomegalovirus, adenovirus, adeno-associated virus, baculovirus, parvovirus, retrovirus, vaccinia, poxvirus, and the like), algae, protozoans, protists, plants, bryophytes, and the like, and any combination of any of the foregoing.

In some aspects of the invention, the quantification of the target nucleic acids may be done sequentially, while in other aspects, it may be desirable to quantify multiple target nucleic acids simultaneously. For example, a given blood sample could first be tested for the level of MTB in the blood, followed by HIV or both could be quantified at the same time.

The methods of invention also can be used to monitor disease outbreak, progression, spread, or one or more other epidemiological statistics within, among, or between one or more global populations, including, without limitation, the spread of mycobacterial infections, the development of clinical signs of tubercular disease, and/or comorbidity with one or more additional infections such as, without limitation, wasting syndrome, Dengue fever, ebola, HIV, SARS, and one or more bacterial or viral infections, including, without limitation, pneumonias, influenzas, and the like. In certain embodiments, the samples will preferably be of mammalian origin, and more preferably of human origin.

Methods of the invention can also be adapted for high-throughput analysis by mechanizing the mixing and analysis of samples and amplification products. In such high-throughput analysis, samples can be compared with one or more controls and with immediate reports by computer analysis. High-throughput screening (HTS) is a method for scientific experimentation especially useful in drug discovery. HTS of the invention uses multiwall plates and vessels (e.g. microtiter plates), robotics, data processing and control software, liquid handling devices, and sensitive detectors that allows for the analysis of thousands to millions of sample nearly simultaneously. Through this process the effectiveness of pharmaceutical compounds, antibodies, sequences or genes that modulate a particular infections condition can be readily and rapidly identified. The results of these experiments provide starting points for drug design and for understanding the interaction or role of a particular biochemical process. HTS assays provide integration of both experimental and computational approaches for data analysis and quality control which typically include a selection of effective positive and negative controls. In a typical HTS experiment, a clear distinction between a positive control and a negative reference such as a negative control is an index for good quality.

Another embodiment of the invention utilizing the compositions and apparatus disclosed herein comprises the detection and quantitation of both DNA and RNA sequences in multiple biological samples obtained from the same individual over time to assess an infection and/or to assess the effectiveness of a treatment. Samples can be obtained from patients over time (e.g., hours, days, weeks), including after administration of a pharmaceutical agent or other care for the suspected disease or disorder. PCR or RT-PCR utilizing the compositions and/or apparatus of the invention monitors the presence or absence and/or quantity of an infectious agent by detecting and determining the presence and quantity of a target DNA or RNA sequence of the genome of the infections agent. Using the same or similarly collected biological samples, RT-PCR is performed to determine the presence or absence and/or quantity of RNA, and specifically mRNA of the infectious agent. The presence of the genomic sequence will determine the presence of the infectious agent, but the presence of genomic sequences can be from live or dead cells and/or microbes. Determining the presence and/or quantity of mRNA is an assessment of the active infection of live cells or organisms. Accordingly, the ratio of DNA or genomic sequence vs. mRNA sequence present in each sample over time presents a picture of the progression of the disease and/or the effectiveness of a treatment. An increasing ratio of genomic sequences vs. mRNA sequences over time or as compared to a control or an initial assessment or base ratio (e.g., DNA:mRNA begins at 1:1 and increases to 1:2, 1:3 or even greater), means that the amount of mRNA as compared to DNA is increasing. In other words detected greater amounts of mRNA in samples obtained over time indicates a strengthening or worsening infection. A decreasing ratio of genomic sequences vs. mRNA sequences over time or as compared to a control or an initial assessment or base ratio (e.g., DNA:mRNA begins at 1:1 and decreases to 2:1, 3:1 or even less), meaning that the amount of mRNA as compared to DNA is decreasing. Accordingly, the infection is resolving or abating and the number of active or living infectious agents present over time is reducing. Preferably assessments are performed on biological samples obtained over multiple periods of time from a single patient (e.g., any combination of hourly, every other hour, every 6, 12 or 18 hours, every day, weekly, etc.) over a set period of time (e.g., over 1, 2, 3, 4, 5, 6, 7, 8, 9, 10, 11, 12, 13 or 14 days, 1, 2, 3 or 4 weeks, 1, 2, 3, or 4 months), which can be repeated as often as desired, to obtain an assessment of a resolving or worsening infection. By obtaining samples over time, such as before and after treatment has begun, and monitoring DNA and mRNA detected, the progress of the infection, effectiveness of a treatment can be monitored and assessed.

Specimen/Sample Collection Compositions

Collections composition can be prepared from concentrated solutions of ingredients or collections of ingredients that are diluted with, preferably nuclease-free water before use. Alternatively, collection compositions may be diluted upon mixing with a biological sample. Preferred embodiments of collection compositions contain: (i) a chaotrope which is preferably guanidine thiocyanate, guanidine isocyanate, guanidine hydrochloride, or any combination thereof; (ii) a detergent which is preferably sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof; (iii) a reducing agent which is preferably 2-mercaptoethanol, tris (2-carboxyethyl) phosphine, dithiothreitol, dimethylsulfoxide, or any combination thereof; (iv) a chelator which is preferably ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof; (v) a buffer which is preferably tris(hydroxymethyl) aminomethane, citrate, 2-(N-morpholino)ethanesulfonic acid, N,N-Bis(2-hydroxyethyl)-2-aminoethanesulfonic acid, 1,3-bis(tris(hydroxymethyl) methyl amino)propane, 4-(2-hydroxyethyl)-1-piperazine ethanesulfonic acid, 3-(N-morpholino) propanesulfonic acid, bicarbonate, phosphate, or any combination thereof, and optionally (vi) a matrix material such as, for example, a resin or acrylic matrix material in the form of, for example, beads. Matrix materials, when present, may be magnetic or otherwise isolatable and may include modifications that allow for capture of nucleic acids or other molecules.

Preferred formulations that are at ready-to-use concentrations include: (a)(i) about 3 M guanidine thiocyanate; (ii) about 1 mM TCEP; (iii) about 10 mM sodium citrate; (iv) about 0.5% N-lauroyl sarcosine; (v) about 0.0002% silicone polymer; (vi) about 100 mM 2-amino-2-hydroxymethyl-propane-1,3-diol (TRIS); and (vii) about 0.1 mM EDTA; or (b) (i) about 3 M guanidine thiocyanate; (ii) 1 mM TCEP; about 10 mM sodium citrate; (iii) about 0.5% N-lauroyl sarcosine, sodium salt; (iv) about 0.0002% of a silicone polymer; (v) about 100 mM TRIS; (vi) about 0.1 mM EDTA; and (vii) about 10% to about 25% ethanol (vol./vol.). Formulation may be concentrated and diluted before use and/or diluted with the addition of the biological sample.

Because of the remarkable effectiveness of the formulations of collection compositions in readily killing, and lysing the cells, denaturing the proteinaceous cellular components and inactivating enzymes such as endogenous and exogenous nucleases that are deleterious to the preservation of intact nucleic acids, the inventors have demonstrated that in certain instances, substantially all of the microorganisms present in a sample are killed and/or lysed within the first few minutes it is contacted with the composition. In some instances, the killing and lysing of the cells is substantially or totally complete within about 3 or about 4 or about 5 or so minutes of contacting the sample with the composition. Likewise, in other instances, contacting the sample with the composition for a period of about 6, or about 7, or about 8, or about 9, or about 10 minutes or so is sufficient to substantially kill and/or lyse all of the pathogens that may be present in the collected sample. Likewise, substantially all of the proteins, enzymes, nucleases, and the like liberated from the lysed cells present in a sample are substantially all or all inactivated and/or denatured within only a few minutes of contacting the sample with the composition. Preferred collection compositions include those listed in Table 1 and compositions obtained commercially such as PRIME-STORE™ (Longhorn Vaccines and Diagnostics, LLC, Bethesda, Md.).

The collection composition improves conventional specimen collection, ensures lysis killing of the of any microbial pathogens contained therein, and facilitates safe and effective transport and storage of such samples from the point of collection to the point of identification and assay. Moreover, the molecular transport media compositions disclosed herein facilitate stabilization of nucleic acids liberated from the collected microorganisms, as well as maintain the fidelity and preserve the integrity of the liberated nucleic acids for extended periods of time, even under ambient, or less-than-ideal storage conditions.

The collection compositions of the present invention provides collection and preservation formulation that lyses biological pathogens, stabilizes the liberated nucleic acids (both RNA and DNA), and preferably at least substantially maintains, and preferably entirely maintains, the integrity of the collected polynucleotides such that at least a first portion of which is readily available, and ideally suited for downstream molecular bacterial load analysis of the nucleic acids contained within the collected specimen.

The "one-step" isolation/storage/transport formulations disclosed herein advantageously accomplish at least one or more, and preferably, all of, the following principal functions: inactivation or killing of pathogens within the sample; lysis of cells and release of nucleic acids from within the cells; inactivation of cellular enzymes, including endogenous and exogenous nucleases, to prevent degradation of the liberated nucleic acids; facilitation of facile collection and safe handling/transport of the sample of isolated polynucleotides at ambient temperatures for extended periods of time without the need for refrigeration or conventional sub-zero storage temperatures; effective stabilization of the nucleic acids during subsequent handling, transport and/or storage of the sample; and preservation and/or maintenance of the integrity of at least a first portion of the population of polynucleotides contained therein for a time sufficient to permit molecular characterization and identification of at least a first nucleic acid segment contained therein.

In particular aspects as described herein, and particularly when performing the method for the analysis of specimens that are acquired in either remote or "field" sites, the collection compositions of the present invention preferably stabilize the collected biological sample for at least a period of time sufficient to facilitate subsequent molecular analysis, without substantial degradation or loss of at least a first population of nucleic acids obtained from the collected sample. Preferably, the collection compositions herein facilitate collection/transport/storage of the blood specimens collected therein for extended periods of time (from a few hours to a few days, or even a few weeks or months or more) at ambient environmental temperatures, such that the collected samples do not require refrigeration and/or freezing in order to preserve them for subsequent molecular testing. More preferably still, the collection composition formulations disclosed herein stabilize and preserve the collected nucleic acids in sufficient fashion to permit subsequent amplification and quantification of at least a first nucleic acid sequence from at least a first microbial pathogen present in the collected sample.

The collection composition formulations described herein further optionally include at least a first internal positive control (IPC) to facilitate improved recovery of the microbial-specific polynucleotides, and to permit determination of sequence fidelity and preservation of the collected specimen. Exemplary known polynucleotide sequences may be present in the collection reagent at the time of specimen collection, and the subsequent analysis of this known quantity of IPC may be used to accurately monitor the fidelity of the population of polynucleotides throughout the collection/transport/analysis phases of the described identification methods.

In one embodiment, the collection and PCR-ready compositions disclosed herein may be formulated such that the entire specimen collection and nucleic acid amplification/detection process may be accomplished in remote, field, battlefield, rural, or otherwise non-laboratory conditions without significantly limiting the fidelity, accuracy, or efficiency of the amplification/detection methodology. Such aspects of the invention provide particular advantages over conventional laborious isolation/collection/transport/storage/analysis protocols that require several days to several weeks to achieve, and must often be conducted under conditions that require refrigeration or freezing of the sample and/or assay reagents in order to properly complete the analysis. By providing reagent mixtures that include a mixture with all of the necessary isolation, storage, and polynucleotide stabilization components, as well as mixtures with all of the necessary reagents for amplification of selected target nucleotides (including, without limitation, the amplification primers and detection probes described herein, alone or in combination with one or more PCR buffers, diluents, reagents, polymerases, detectable labels, and such like), in a shelf-stable, ambient-temperature facile reagent mix, significant cost savings, time-reduction, and other economies of scale may be achieved using the present invention as compared to many of the conventional oligonucleotide probe-based thermal cycling assays commercially available.

The compositions and methods of the present invention are directed to the collection of a clinical or veterinary specimen or a forensic or environmental sample collection system and may include one or more collection tools and one or more reagents for efficiently: 1) obtaining a high yield of suitable specimen beyond what is currently available in the art; 2) inactivating potentially infectious biological pathogens, such as members of the *M. tuberculosis* complex, so that they are no longer viable and can be handled; shipped, or transported with minimal fear of pathogen release or contamination; or 3) effectively stabilizing and preserving lysed 'naked' RNA/DNA polymers from hydrolysis or nuclease degradation for prolonged periods at ambient temperatures until samples can be processed at a diagnostic laboratory, and preferably for achieving two or more, or all three, of these goals. The collection solutions of the present invention provide the following benefits: inactivation, killing, and/or lysis of microbes, viruses, or pathogens; destruction and/or inactivation of exogenous or endogenous nucleases, including, without limitation, RNase and/or DNase; compatibility with a variety of conventional nucleic acid extraction, purification, and amplification systems; preservation of RNA and/or DNA integrity within the sample; facilitation of transport and shipping at ambient or tropical temperatures, even over extended periods of time, or extreme temperature variations; and suitability for short— (several hours to several days), intermediate—(several days to several weeks), or long—(several weeks to several months) term storage of the isolated nucleic acids.

PCR-Ready Compositions

PCR-Ready compositions comprise aqueous composition that allow for primer-dependent amplification reaction and are compatible with Collection compositions. Preferred PCR-Ready compositions include: (a) a buffer; (b) an osmolarity agent; (c) an albumin protein; (d) a chelator; (e) a salt; (f) a pair of sequence-specific amplification primers (e.g., pathogen specific, gene specific, sequence specific), wherein each of the first and second primers specifically hybridize to a first, and a second distinct target region; (g) at least one primer-dependent amplification reaction-capable thermostable polymerase; and (h) a plurality of deoxynucleoside triphosphates, each present in an amount sufficient to enable PCR amplification. Optionally compositions may include a pathogen-specific oligonucleotide detection probe comprising a first detectable label that specifically hybridizes to a third sequence region. Compositions that are thermal-cycling ready (e.g., PCR ready) may be maintained in ready-to-use concentrations, or in concentrated forms such as, for example, 2×, 5×, 10×, 20×25×, 30×, or greater as convenient or necessary for the particular application. Preferred PCR-Ready compositions include those formulations listed in Table 2 and compositions obtained commercially such as PRIMEMIX™ (Longhorn Vaccines and Diagnostics, LLC, Bethesda, Md.).

In preferred embodiments the PCR-ready composition includes, (a) a buffer which is preferably tris(hydroxymethyl)aminomethane (TRIS); (b) a polymerase chain reaction osmolarity agent which is preferably N,N,N-trimethylglycine (betaine), dimethyl sulfoxide (DMSO), foramide, glycerol, nonionic detergents, bovine serum albumin (BSA), polyethylene glycol, tetramethylammonium chloride, or any combination thereof; (c) an albumin protein which is preferably BSA, HAS or any mammalian albumin; (d) a chelator which is preferably ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof; and (e) a salt which is preferably potassium chloride, magnesium sulfate, potassium glutamate, or any combination thereof, and the pair of PCR primers which preferably include: (i) a first oligonucleotide primer of 18 to about 30 nucleotides in length that preferably includes at least a first sequence region that consists of a sequence that is at least 95% identical to the pathogen-specific nucleic acid sequence; and (ii) a second oligonucleotide primer of 18 to about 30 nucleotides in length that preferably includes at least a first sequence region that consists of a sequence that is at least about 90% identical, preferably at least about 95% identical to, and more preferably, at least about 98% identical the pathogen-specific nucleic acid sequence, or a complement thereof.

The pathogen-specific oligonucleotide detection probe preferably is from 24 to about 35 nucleotides in length, and more preferably includes at least a first sequence region that consists of a sequence that is at least 85% identical, at least 90% identical, at least 95% identical, or at least 98% or greater identical to at least a first contiguous nucleic acid sequence from a pathogen-specific sequence, or a complement thereof. The PCR-ready composition may further optionally include one or more internal reference dyes compatible with a polymerase chain reaction (e.g., ROX), such as those that include one or more fluorophores, one or more quenchers, one or more reporter molecules, one or more nucleic acid intercalating agents, or any combination thereof.

In illustrative embodiments, the composition at ready-to-use concentrations preferably includes (a) about 50 mM of TRIS; (b) about 70 mM of potassium chloride; (c) about 3 mM of magnesium sulfate; (d) about 45 mM betaine; (e) about 0.03 µg/mL of bovine serum albumin; (f) about 0.1 mM of EDTA; (g) about 0.01 µM to about 1 µM of dye; (h) about 4 µM of a first oligonucleotide primer of 18 to about 30 nucleotides in length; (i) about 4 µM of a second oligonucleotide primer of 18 to about 30 nucleotides in length; (j) about 6 µM of a pathogen-specific oligonucleotide detection probe of 24 to about 35 nucleotides in length; (k) about 1 unit of Taq polymerase; and (l) about 0.2 mM of deoxynucleoside triphosphates.

The detectable label may preferably include one or more radioactive labels, one or more luminescent labels, one or more chemiluminescent labels, one or more fluorescent labels, one or more phosphorescent labels, one or more magnetic labels, one or more spin-resonance labels, one or more enzymatic labels, or any combination thereof. Exemplary detectable labels include, without limitation, fluorescein, 6-carboxyfluorescein (6-FAM), 6-carboxyfluorescein-N-succinimidyl ester (6-FAMSE), a VIC dye, or any combination thereof. Preferably, to this formulation a sufficient amount of primers and probe are added so as to amplify and detect the desired target. When used within PrimeMix®, this 10× buffer solution is diluted to about 0.5× to about 2×, preferably, about 1×.

PCR-Ready compositions can include one or more microbial-specific nucleic acid sequences and: (i) one or more buffers (each preferably present in the composition in an amount from about 1 mM to about 1M); (ii) one or more osmolarity agents or albumin proteins at least one of which comprises betaine (each preferably present in the composition in an amount from about 1 mM to about 1M); (iii) one or more chelators (each preferably present in the composition in an amount from about 0.01 mM to about 1 mM); (iv) one or more reference dyes (each preferably present in the composition in an amount from about 0.01 µM to about 50 mM, more preferably about 0.02 µM to about 1 µM); and (v) one or more salts (each preferably present in the composition in an amount from about 50 mM to about 1 M); and a first pair of pathogen-specific amplification primers. In some embodiments, the composition further includes a pathogen-specific probe. In one embodiment, the reference dye is present in an amount of about 0.01 µM to about 1 µM. Preferably the composition includes one or more salts. The salts are preferably potassium chloride, magnesium chloride, magnesium sulfate, potassium glutamate, or any combination thereof. Preferably, the concentration of salt in the composition is between about 0.5 mM and about 50 mM.

The inclusion of one or more buffers is desirable to control the pH of the formulations which stabilizes the nucleic acids and the enzymes. A preferred pH range is from about 6.0 to about 9.5, preferably between about 6.5 and about 8.0, and more preferably between bout 6.5 and about 7.5. Preferably, the pH of the buffer and/or the overall composition is within one unit of the pKa of the buffer, more preferably within about 0.5 units, more preferably within about 0.2 units and more preferably within about 0.1 units, all as measured at a selected temperature, preferably an ambient temperature. Exemplary buffers include, without limitation, tris(hydroxymethyl) aminomethane (Tris), citrate, 2-(N-morpholino)ethanesulfonic acid (MES), N,N-Bis (2-hydroxyethyl)-2-aminoethanesulfonic acid (BES), 1,3-bis(tris(hydroxymethyl) methylamino)propane (Bis-Tris), 4-(2-hydroxyethyl)-1-piperazineethanesulfonic acid (HEPES), 3-(N-morpholino)propanesulfonic acid (MOPS), N,N-bis(2-hydroxyethyl) glycine (Bicine), N-[tris(hydroxymethyl)methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, or any combination thereof. In a preferred embodiment, the buffer includes TRIS.

At least a first osmolarity agent can be used within the method to optimize reaction conditions, especially when a high content of guanine and cytosine are present in the sequences, and can include, without limitation, betaine, trimethylglycine, glycine betaine, dimethylsulfoxide (DMSO), foramide, deoxyinosine, glycerine, 7-deaza deoxyguanosine triphosphate, or sodium hydroxide, or any combination thereof.

Exemplary chelators include, without limitation, ethylene glycol tetraacetic acid (EGTA), hydroxyethylethylenediaminetriacetic acid (HEDTA), diethylene triamine pentaacetic acid (DTPA), N,N-bis(carboxymethyl)glycine (NTA), ethylenediaminetetraacetic (EDTA), citrate anhydrous, sodium citrate, calcium citrate, ammonium citrate, ammonium bicitrate, citric acid, diammonium citrate, potassium citrate, magnesium citrate, ferric ammonium citrate, lithium citrate, or any combination thereof. In preferred embodiments, the chelator includes EDTA, a citrate, or a combination thereof. In a more preferred embodiment, the chelator includes EDTA.

At least a first reference dye, preferably an inert chemical, can optionally be used within the method to normalize the results obtained when using fluorescent compounds, such as those used in FRET technologies. The reference dye, when included, can provide an internal reference to which the reporter dye signal can be normalized. Such a reference dye can include, without limitation, passive reference dyes such as fluorescein, 5-carboxy-X-rhodamine and commercial formulations such as ROX™, or a combination thereof. In a more preferred embodiment, the reference dye includes ROX™.

Preferably, the compositions further include the addition of deoxynucleotide triphosphates (dNTPs), such as deoxyadenosine triphosphate, deoxyguanosine triphosphate, deoxycytidine triphosphate, deoxythymidine triphosphate, or deoxyurosine triphosphate, or a combination thereof, in an amount from about 0.1 mM to about 50 mM.

The compositions of the invention can further include one or more additional compounds or reagents including, but not limited to, albumin. Albumin refers generally to any protein that is water soluble, is moderately soluble in concentrated salt solutions, and experiences heat denaturation. Albumins are commonly found in blood plasma and are unique from other blood proteins in that they are not glycosylated. Preferably the albumin is bovine serum albumin (BSA), magnesium sulfate, water and acids or bases, such as hydrochloric acid and sodium hydroxide. The acids or bases can be added to the final solution to adjust the pH. Preferably, BSA is added in a concentration of about 0.01 µg/µL to about 0.5 µg/µL.

The compositions of the invention can further include one or more polymerases. The one or more polymerases can include, but are not limited to, Taq polymerase, and high fidelity polymerases. Preferably, the one or more polymerases are present in an amount of about 1 U of enzyme to about 10 through about 50 µL of final solution.

In particular embodiments, the composition will further preferably include at least a first oligonucleotide detection probe that includes a radioactive, luminescent, chemiluminescent, fluorescent, enzymatic, magnetic, or spin-resonance label, or combination thereof. Fluorescent labels can include fluoroscein, 6-carboxyfluorescein (6-FAM), or 6-carboxyfluorescein-N-succinimidyl ester (6-FAMSE), or the like, or a combination thereof. Preferred primer and/or probe concentration for each nucleic acid is between about 1 pmol and about 10 µM.

The invention further provides methods for quantitating pathogen-specific nucleic acid segments in a population of polynucleotides obtained from a blood sample, the method including: (a) performing at least one thermal cycling step, wherein the cycling comprises at least a first amplifying step and at least a first hybridizing step, wherein the at least a first amplifying step comprises contacting a population of polynucleotides obtained from a biological sample suspected of containing a pathogen-specific nucleic acid segment with a composition that comprises at least a pair of distinct, independently-selected, pathogen-specific amplification primers, a polymerase, a first osmolarity agent comprising betaine, optionally (but preferably) at least a first reference dye, and a plurality of deoxynucleoside triphosphates to produce a pathogen-specific amplification product when a pathogen-specific nucleic acid segment is present in the sample; and (b) detecting the presence of the amplification product by contacting the amplification product with a pathogen-specific oligonucleotide detection probe comprising a first detectable label, wherein the presence of a labeled hybridization product is indicative of the presence of one or more pathogen-specific nucleic acid segments in the population of polynucleotides, wherein the pair of distinct, independently-selected, pathogen-specific amplification primers comprises a first oligonucleotide primer of 18 to about 30 nucleotides in length, and a second oligonucleotide primer of 18 to about 30 nucleotides in length, wherein each of the first and second primers specifically hybridize to a first, and a second distinct sequence region, respectively, within the pathogen-specific sequence, or the complement or reverse complement thereof.

A further embodiment of the invention includes methods for quantifying of a microbial sequence that includes obtaining genomic nucleic acid from a biological sample and assaying the genomic material by adding the nucleic acid to the reagent mix of one or more microbe-specific primers, probes, or enzymes, or a combination thereof, wherein the mix is substantially stable at room temperature and is adapted for use with a PCR device. In another embodiment, the PCR device includes fluorescence detection equipment for real-time PCR detection.

In a further embodiment, the invention provides a method for detecting the quantity of a Mycobacterial-specific nucleic acid segment, and in particular aspects, provides a method for quantitating the presence or absence of a particular type, subtype, or strain of *M. tuberculosis*. In exemplary embodiments, the invention provides a method of identifying Mycobacterial species and strains that contain one or more IS6110-specific nucleic acid segments in a population of polynucleotides that is preferably obtained from a biological sample.

In another aspect, the present invention provides a method for rapidly detecting in a biological sample, a particular polynucleotide sequence, such as that of the *Mycobacterium*-specific IS6110 sequence. In an overall and general sense, this method comprises amplification of a population of nucleotides suspected of containing the particular sequence using conventional methods such as PCR and forward and reverse primers that are specific for the target sequence, hybridization of a specific probe set with the resulting single-stranded PCR product, performing melting curve analysis and analyzing the $T_m$ change of the hybrid of the single-stranded PCR product with the hybridization probes.

The label on the probe can include, without limitation, radioactive, luminescent, chemiluminescent, fluorescent, enzymatic, magnetic, or spin-resonance labels known to those of ordinary skill in the molecular arts. In illustrative embodiments, the labeled probe contains at least a first minor groove binder. One such method for the detection of polynucleotides using a labeled "probe" sequence utilizes the process of fluorescence resonance energy transfer (FRET). Exemplary FRET detection methodologies often involve pairs of fluorophores comprising a donor fluorophore and acceptor fluorophore, wherein the donor fluorophore is capable of transferring resonance energy to the acceptor fluorophore. In exemplary FRET assays, the absorption spectrum of the donor fluorophore does not substantially overlap the absorption spectrum of the acceptor fluorophore. As used herein, "a donor oligonucleotide probe" refers to an oligonucleotide that is labeled with a donor fluorophore of a fluorescent resonance energy transfer pair. As used herein, "an acceptor oligonucleotide probe" refers to an oligonucleotide that is labeled with an acceptor fluorophore of a fluorescent resonance energy transfer pair. As used herein, a "FRET oligonucleotide pair" will typically comprise an "anchor" or "donor" oligonucleotide probe and an "acceptor" or "sensor" oligonucleotide probe, and such pair forms a FRET relationship when the donor oligonucleotide probe and the acceptor oligonucleotide probe are both hybridized to their complementary target nucleic acid sequences. Acceptable fluorophore pairs for use as fluorescent resonance energy transfer pairs are well known to those of ordinary skill in the art and include, but are not limited to, fluorescein/rhodamine, phycoerythrin/Cy7, fluorescein/Cy5, fluorescein/Cy5.5, fluorescein/LC Red 640, and fluorescein/LC Red 705, and the like.

In the regular practice of the method, one may also perform the cycling step on one or more "negative" and/or "positive" control sample(s) as is routinely done in the molecular genetic assay arts to ensure integrity, fidelity, and accuracy of the method. The use of such controls is routine to those of ordinary skill in the art and need not be further described herein. Likewise, in the practice of the invention, it may also be desirable to incorporate one or more known "internal positive controls" (IPCs) into the population of polynucleotides to be isolated, to further ensure the integrity, fidelity, and/or accuracy of the disclosed method.

In certain embodiments, the addition of nucleic acids (e.g., RNA and/or DNA) is contemplated to be beneficial for a variety of purposes and applications of the disclosed methods: a) as a "carrier" (The addition of small amounts of supplemental RNA/DNA has been previously been shown to augment/increase the overall yield of samples/specimens, particularly original specimens that may contain low amounts of target, i.e., cells, viruses, bacteria); b) as an IPC for downstream molecular processes and to track or monitor the fidelity of the nucleic acid preparation from sample collection to detection; and c) for comparison to a 'calibrator' for downstream quantitative analysis, e.g., qRT-PCR and the like. In such embodiments, one or more known or "control" nucleic acids could be added to the compositions in a final concentration of from about 1 ag to about 1 mg, more preferably from about 1 fg to about 1 µg, and more preferably still, from about 1 pg to about 1 ng.

PCR reactions of the invention can be performed en mass using semiconductor sequencing and/or ion torrent sequencing for the rapid analysis and assessment of amplification products produced from genomic and mRMA sequences. As is believed to clear to those skilled in the art, semiconductor sequencing can be performed rapidly on multiple samples simultaneously and the results collated to rapidly provide an assessment of an infection.

The invention provides an isolated single-stranded (ss) or double-stranded (ds) RNA, DNA, PNA, or hybrid thereof that is useful: (a) as a carrier molecule for aiding in the recovery of polynucleotides from a biological sample suspected of containing nucleic acids, and/or (b) as an IPC (i.e., a "known," "reporter," "control," "standard," or "marker") sequence to monitor the integrity and fidelity of specimen collection and polynucleotide isolation/stabilization. In certain embodiments, the invention provides an isolated ds-RNA, ds-DNA, ds-PNA, or a hybrid thereof that is useful as a carrier molecule and/or an IPC. In other embodiments, the invention provides an isolated ssRNA, ssDNA, ssPNA, or a hybrid thereof that is useful as a carrier molecule and/or as an IPC sequence. In exemplary embodiments, the invention provides an isolated ssRNA molecule that is useful as both a carrier molecule and an IPC sequence or quantitator molecule.

Such molecules can be isolated from natural sources, prepared in the laboratory, or alternatively, a hybrid containing both native- and non-native sequences. As noted herein, because the compositions of the invention are particularly useful for the isolation and characterization of biological specimens obtained from mammalian (and in particular, human) sources that are suspected of containing polynucleotides of pathogen-origin, it is preferable that the sequence(s) employed as carrier and/or positive control compounds substantially contain a primary nucleotide sequence that is not ordinarily found within the genome of a mammal, or within the genome of an organism that is pathogenic to such a mammal. Exemplary mammals include, without limitation, bovines, ovines, porcines, lupines, canines, equines, felines, ursines, murines, leonines, leporines, hircines, and non-human primates.

Preferably, this non-mammalian, non-pathogen-specific carrier/reporter sequence is not cross-reactive, i.e., does not substantially, or preferably, does not, hybridize to, mammalian or pathogen-specific sequences, and as such, non-coding, non-degenerate (i.e., nonsense) sequences are particularly preferred in the formulation of control/carrier sequences to minimize hybridization of the control/carrier sequence to a member of the isolated population of polynucleotides obtained from the collected specimen. Exemplary carrier/control sequences therefore, do not substantially, or preferably, does not, bind (e.g., hybridize under stringent hybridization conditions) to a population of polynucleotides isolated from a mammalian genome, or to a population of polynucleotides isolated from the genome of a bacterium, fungus, virus that is pathogenic to a mammal. Exemplary stringent hybridization conditions known to those of ordinary skill in the art include, without limitation, (a) pre-washing in a solution containing about 5×SSC, 0.5% SDS, and 1.0 mM EDTA (pH 8.0); (b) hybridizing at a temperature of from about 60° C. to about 70° C. in 5×SSC overnight; and (c) subsequently washing at about 65 to about 70° C. for 20 min. with each of 2×, 0.5× and 0.2×SSC containing 0.1% SDS), or equivalent hybridization conditions thereto.

Kits of the Invention

Another embodiment of the invention comprises kits for microbial quantification of blood and other biological sample. Preferably the kits include one or more of the compositions disclosed herein, and instructions for using the kit in the detection of one or more pathogen-specific nucleic acid segment in an aqueous sample. Kits may further include (typically in a separate, distinct container), a first collection composition that comprises: a) one or more chaotropes; b) one or more detergents; c) one or more reducing agents; d) one or more chelators; and e) one or more surfactants, each present in an amount to substantially kill or lyse one or more pathogenic or infected cells, or to denature or inactivate one or more proteins, enzymes, or nucleases liberated there from when placed in the composition for an effective amount of time. In certain embodiments, the kit may also further include (preferably within the collection composition) a known quantity of at least a first internal positive control nucleic acid segment (and preferably one of from about 50 to about 500 nucleotides in length), wherein the internal positive control nucleic acid segment does not substantially hybridize (and preferably, does not specifically hybridize) to the genomic nucleic acids of the host from which the sample was obtained, nor to genomic nucleic acids of the one or more microbiological pathogens suspected within the sample. As noted herein, such kits may also further optionally include one or more extraction apparatuses for isolating and purifying the population of polynucleotides from the lysed/liberated/denatured sample contacted with the formulation of the collection composition. Such an extraction apparatus may be a portable, bench-top, or even a handheld device that preferably includes: (i) a filtration vessel that has at least one receiving end and that comprises a membrane filter adapted to bind the population of polynucleotides thereto, wherein the membrane filter is disposed at least substantially across a width of the filtration vessel and at least partially therein; and (ii) a volume-dispensing mechanism adapted to controllably dispense and forcibly inject an amount of liquid operably associated with the filtration vessel to filter the liquid there through; and b) instructions for using the extraction apparatus to obtain the population of purified polynucleotides from an aqueous sample suspected of comprising at least a first pathogen.

In one embodiment, a method of collecting a biological sample suspected of containing at least a first population of polynucleotides isolated from a pathogen includes: placing the biological sample in a first collection device that contains at least a first solution comprising a) one or more chaotropes; b) one or more detergents; c) one or more reducing agents; d) one or more chelators; and e) one or more surfactants, each present in an amount sufficient to denature one or more proteins, or inactivate one or more nucleases; wherein the collection solution kills, inactivates or decontaminates any pathogens that are present in the specimen for safe handling and transport; and wherein the integrity of the population of polynucleotides is at least substantially maintained and the population of polynucleotides remains substantially non-degraded when the collection solution containing the population of polynucleotides is stored at a temperature of about 10° C. to about 40° C. for a period of about 1 to about 42 days prior to extracting the population of polynucleotides from the collection solution.

The population of polynucleotides obtained from the biological sample is further analyzed. The kits also comprise a reagent mix for quantifying of a microbial sequence, the reagent mix including one or more microbe-specific primers, probes, or enzymes, or a combination thereof, present in a mixture that is at least substantially stable at ambient temperature and is adapted and configured for use with a polymerase chain reaction (PCR) device. The reagent mix can be used to quantitate microbial sequences, such as a pathogen, bacterial or viral sequences, or combination thereof.

Reagent mixture incorporating the aforementioned primers and probes, and kits comprising such compositions for performance of a thermal cycling amplification method. In one embodiment, the invention provides a nucleic acid amplification kit for microbial quantification that generally includes, in a suitable container, a pathogen-specific oligonucleotide amplification primer set as described herein, and instructions for using the primer set in a PCR amplification of a population of polynucleotides obtained from a biological sample or specimen. Such kits may further optionally include, in the same, or in distinct containers, an oligonucleotide detection probe that specifically binds to the amplification product produced from PCR amplification of a population of polynucleotides obtained from a biological sample or specimen that contains, or is suspected of containing, a pathogen-specific nucleic acid segment. Such kits may also further optionally include, in the same, or in a distinct container, any one or more of the reagents, diluents, enzymes, detectable labels (including without limitation, one or more radioactive, luminescent, chemiluminescent, fluorescent, enzymatic, magnetic, or spin-resonance labels), dNTPs, and such like that may be required to perform one or more thermal cycling amplifications of a population of polynucleotides as described herein.

Kits may also include one or more extraction devices or apparatuses, as described above, to facilitate the isolation or separation of the nucleic acids from the collected biological sample. Kits of the invention may also optionally further include one or more portable, ruggedized, or field-employable thermal cycling, PCR amplification systems and/or one or more systems, devices, or instruments to facilitate detection, quantitation, and/or distribution of the detectable label(s) employed for visualization of the amplification products produced during the practice of the method.

The diagnostic reagents and kits of the present invention may be packaged for commercial distribution, and may further optionally include one or more collection, delivery, transportation, or storage devices for sample or specimen collection, handling, or processing. The container(s) for such kits may typically include at least one vial, test tube, flask, bottle, specimen cup, or other container, into which the composition(s) may be placed, and, preferably, suitably aliquotted for individual specimen collection, transport, and storage. The kit may also include a larger container, such as a case, that includes the containers noted above, along with other equipment, instructions, and the like. The kit may also optionally include one or more additional reagents, buffers, or compounds, and may also further optionally include instructions for use of the kit in the collection of a clinical, diagnostic, environmental, or forensic sample, as well as instructions for the storage and transport of such a sample once placed in one or more of the disclosed compositions.

Internal Positive Controls

The collection solutions and methods may further include at least one internal positive control (IPC) to monitor fidelity of the processed samples, to monitor the integrity and fidelity of specimen collection and polynucleotide isolation/stabilization and/or to monitor downstream molecular processes or analysis. Methods include placing at least one IPC nucleic acid segment into the collection solutions of the present invention or combining the IPC nucleic acid segment with the extracted population of polynucleotides to monitor downstream molecular processing of the sample and/or extracted nucleic acid. In some embodiments, the IPC is present as a component of the PrimeStore® solution and, as such is substantially stable, and substantially non-degraded when stored in the solution for extended time periods at ambient temperatures. In these instances, the IPC may be considered part of the population of polynucleotides when extracted from the collection solution.

Preferably, the IPC sequence is not cross-reactive, i.e., does not substantially, or preferably, do(es) not, hybridize to, mammalian or pathogen-specific sequences, and as such, non-coding, non-degenerate (i.e., nonsense) sequences are particularly preferred in the formulation of control/carrier sequences to minimize hybridization of the control/carrier sequence to a member of the isolated population of polynucleotides obtained from the collected specimen. Exemplary carrier/control sequences therefore, do not substantially, or preferably, do(es) not, bind (e.g., hybridize under stringent hybridization conditions) to a population of polynucleotides isolated from a mammalian genome, or to a population of polynucleotides isolated from the genome of a bacterium, fungus, protozoan, virus that is pathogenic to a mammal.

In certain embodiments, the invention provides an isolated single stranded (ss)-RNA, ss-DNA, ss-PNA, double stranded (ds)-RNA, ds-DNA, ds-PNA, or a hybrid thereof, that is useful as an IPC. In preferred embodiments, where the isolation and quantifying of *M. tuberculosis*-complex specific nucleic acid is desired, a single stranded deoxyribonucleic acid segment is used.

Where further molecular processing of the sample or extracted nucleic acid consists of quantifying *M. tuberculosis*-complex specific nucleic acids, the IPC sequences of the present invention should contain at least a first sequence domain that specifically hybridizes (i.e., binds) to a suitably-detectable probe, including, without limitation, molecularly-labeled probes and derivatives thereof. Exemplary labeled probes are those that include radioactive, luminescent, chemiluminescent, fluorescent, enzymatic, magnetic, or spin-resonance labels known to those of ordinary skill in the molecular arts. In preferred embodiments, the probe is labeled with 6-FAM or VIC™ dye. In illustrative embodiments, the labeled probe contains at least a first minor groove binder. In further embodiments, wherein amplification strategies such as PCR will be employed, the IPC sequences of the present invention contain at least a second sequence domain that specifically binds to a forward PCR amplification primer and a third sequence domain that specifically binds to a reverse PCR amplification primer.

The following examples illustrate embodiments of the invention, but should not be viewed as limiting the scope of the invention.

EXAMPLES

Example 1—Analysis of Infection

Exposure to MTB can result in the spread of bacilli to many organ tissues throughout the body, including the blood. In addition, the level of MTB in the blood can reflect the disease severity and state of MTB disease. To assess the ability to detect MTB bacterial loads in the blood, whole blood was collected from mice challenged with MTB, placed and the blood was placed in PrimeStore®.

BALB/c female mice were injected intravenously with 0.2 mls of ethanol killed MTB (approximately $10^5$ CFU/mL). Two anti-MTB opsonophagocytic bactericidal MABs were used to simulate treatment of MTB sepsis. Mouse monoclonal antibodies (MAB LHN-AB9 or LHN-GG9) or control were given IP using 0.3 mls of sterile PBS 24 hours before MTB challenge. To monitor MTB in the blood, mice were bled at 3 time points: immediately after injection with MTB and again at 4 and 24 hours before MTB challenge. Collected blood was placed into citrate tubes and 0.1 ml was transferred into PrimeStore®. Samples were transported at ambient temperature from Gaithersburg, Md. to San Antonio, Tex. DNA was extracted from blood in PrimeStore® and replicate real-time polymerase chain reactions (PCR) were performed using PrimeMix® MTB Complex on an ABI 7500 Instrument.

Blood PCRs on specimens obtained 15 minutes after MTB challenge were positive with an average CT value of 29.8 (range 29.2-30.6). Mice treated with PBS control had MTB detected in the blood by PCR at all time points (at 15 min, 4 and 24 hours post challenge). Mice given anti-TB opsonic MABs cleared the MTB from the blood either by 4 or 24 hours (CT=40).

In this study blood specimens were efficiently transported to a central lab to quantify MTB bacteremia by PCR. In addition, PCR can be used to monitor patient treatment, similar to viral load testing for HIV. Using PrimeStore® to ship specimens safely and rapidly at ambient temperature to a regional facility for PCR MTB bacterial load testing and can provide rural hospitals in sub-Saharan Africa the opportunity to diagnose MTB sepsis determine the severity of disease and monitor treatment.

Example 2—Extraction of Nucleic Acids from Biological Samples

Following collection of the population of polynucleotides from a biological sample, a method of nucleic acid extraction or separation from the collection solution and microorganism debris, such as proteins, lipids and carbohydrates, is performed by phenol/chloroform purification or silica-based methods, and extraction methods based on magnetic glass particles. Compositions and methods used in the present invention are compatible with most, if not all, commercially available nucleic acid extraction compositions and methods, such as, but not limited to PrimeExtract™, QiaAmp® DNA Mini kit (Qiagen®, Hilden, Germany), MagNA Pure 96 System (Roche Diagnostics, USA), and the NucliSENS® easyMAG® extraction system (bioMérieux, France). Generally, the extracted genomic nucleic acid is present in an amount from about 0.1 microliters to about 10,000 microliters, more preferably from about 1 microliter to about 1000 microliters, and more preferably from about 10 microliters to 100 microliters. An exemplary amount of nucleic acid is 25 microliters.

Example 3—Compositions and Methods for Multiplex Analysis of Biological Samples

Reagent mixtures include more than a single pair of amplification primers and a detection probe that is specific for a given target nucleic acid sequence. To quantify two or more different types of pathogens, the composition of the invention is formulated to contain a first pair of amplification primers that specifically bind to a first target region of one pathogen-specific polynucleotide, and a second pair of amplification primers that specifically bind to a first target region of another pathogen-specific polynucleotide.

Alternatively, when it is desirable to determine the presence of two or more different strains, the composition of the invention may be formulated to contain a first pair of amplification primers that specifically bind to a first target region of a particular pathogen-specific polynucleotide, and a second pair of amplification primers that specifically bind to a first target region of a second, distinct pathogen-specific polynucleotide.

Additionally, when it is desirable to determine the presence of one or more additional microorganisms in the blood, i.e., to identify the severity of disease when a patient is co-infected, with more than one bacterial, or fungal, or viral infections, for example, gram-positive and gram-negative bacteria, human immunodeficiency virus, pneumococcus, influenza, hepatitis viruses, *Yesinia pestis, Pseudomonas* sp., *Stenotrophomonas maltophilia, Burkholderia cepacia, Streptococcus* sp., *Moraxella catarrhalis,* Enterobacteriaceae, *Haemophilus* sp., *Staphylococcus* sp., Rhinovirus, Respiratory syncytial virus, Coronavirus, Adenovirus, *Chlamydophila pneumoniae, Mycoplasma pneumoniae, Pneumocystis jiroveci, plasmodium* species and the like.

For detection of the particular amplification product(s) produced from such compositions, the compositions also include a first detection probe that specifically binds to the amplification product produced from the first pair of amplification primers, and a second distinct detection probe that specifically binds to the amplification product produced from the second pair of amplification primers. In such compositions, it is preferable that the two, three or four detection probes present in the formulation be distinct, such that each of the probes (if specifically bound to a target in the resulting amplification mixture) may be individually detectable using conventional methodologies. Such probe distinctiveness is readily achievable in the conventional arts, using, for example, detection probes that include detection moieties that fluoresce at two, three or four distinctly-different wavelengths.

Example 4 DNA/RNA Ratios to Evaluate Live Versus Dead Microbes in Specimens

Figure 2A:
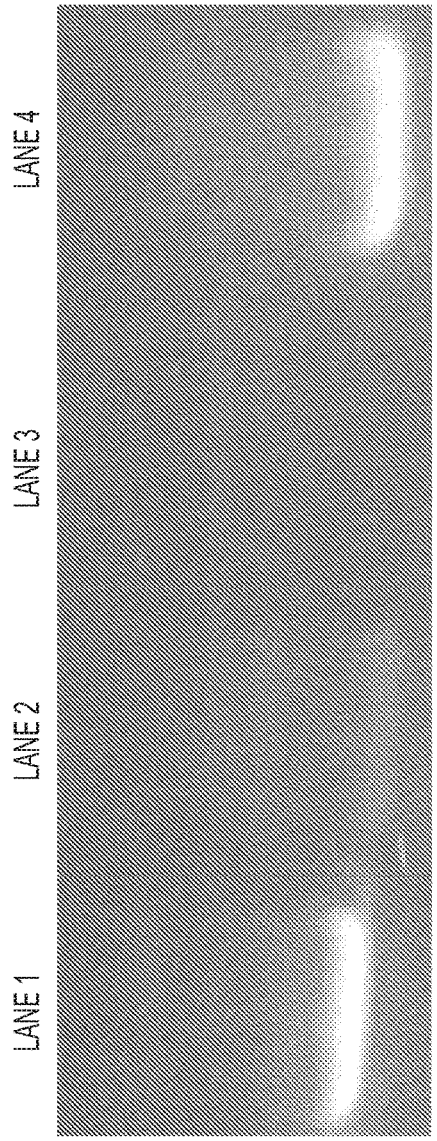
Figure 2B:
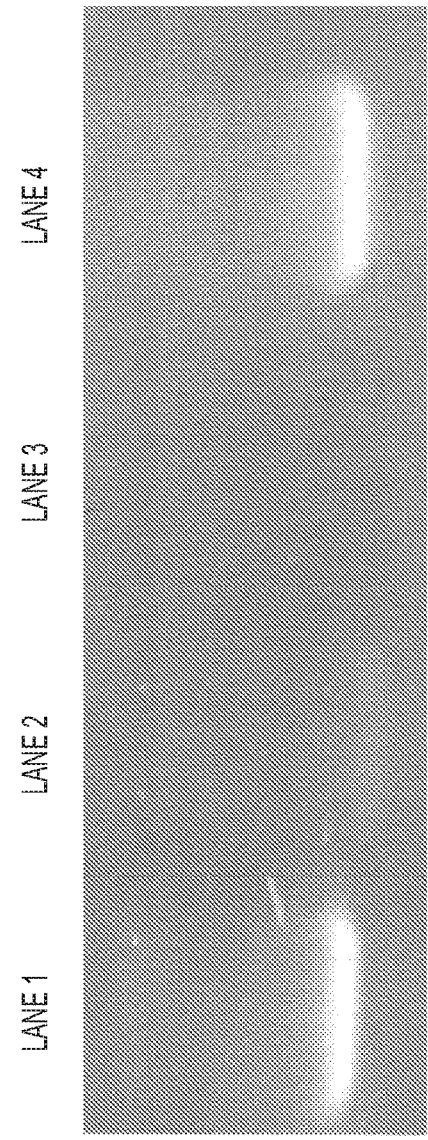

Multi drug resistant MTB (MDR MTB) is an example of bacteria that are becoming resistant to multiple antibiotics. Culture and phenotypic drug sensitivity testing (DST) takes time and for MTB may take 2-3 months to determine if a patient is on effective treatment. PrimeStore MTM (MTM) preserves all nucleic acids from specimens placed in MTM and both RNA and DNA can be quantified using PrimeMix qPCR. For the RNA qPCR, PrimeMix contains specific primers, probes and polymerase (for DNA detection) plus reverse transcriptase to detect the target mRNA. While the presence of a DNA sequence reflects live and dead bacteria, bacterial messenger RNA (mRNA) reflects the presence of live organism. As shown in FIG. 1 and summarized in Table 3, a decreasing ratio of mRNA to bacterial DNA done on sequential specimens (3, 7 and 14 days) shows that the bacteria are being killed by the treatment, or an unchanged ratio demonstrates an ineffective treatment. As shown in FIGS. 2A and 2B, gel electrophoresis (2%) of RT-PCR products from *Mycobacterium tuberculosis* (MTB) total nucleic acids (Lane 1) and RNA (Lane 2) from samples using a 456 base pair fragment of the 85a gene. No template control (NTC; Lane 3) and positive control (Lane 4). The relatively constant amount of DNA in Lane 1 of Samples 1 and 2, as compared to the decreased amount of RNA in Lane 2 of Sample 2 as compared to Sample 1 shows that there is a decreased amount of RNA present in Sample 2 and that the infection is abating.

For MTB, this approach identifies ineffective drug regimens in days, rather than months. Increase in MTB heat shock protein (HSP) mRNA shortly after initiation of treatment for TB indicates MTB *Bacillus* stress and confirms effective treatment regimen after 2-5 days of treatment. In a biphasic manner, the HSP mRNA first goes up (as a response to being damaged and are struggling to survive) and then as the MTB dies the HSP mRNA decreases and the ratio again decreases (mRNA/DNA decreases). By comparing HSP mRNA to a non-HSP mRNA (85a antigen) one sees the HSP go biphasic (up and then down) over the first 2-5 days after effective treatment, but 85a goes steadily down as the bacteria are killed. This provides an early indication of effective therapy, or the lack thereof.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the claims.

TABLE 1

FORMULATION RANGES OF EXEMPLARY COMPONENTS OF COLLECTION COMPOSITIONS

| Reagent | Component Final Concentration Ranges |
|---|---|
| 1. A chaotrope, e.g.: | |
| Guanidine thiocyanate | about 0.5M to about 6M |
| or Guanidine hydrochloride | about 0.5M to about 6M |
| or Guanidine isocyanate | about 0.5M to about 6M |
| 2. An anionic detergent, e.g.: | |
| N-lauroyl sarcosine (inter alia Na salt) | about 0.15% to about 1% (wt./vol.) |
| or Sodium dodecyl sulfate, | Same |
| Lithium dodecyl sulfate, | Same |
| Sodium glycocholate, | Same |
| Sodium deoxycholate, | Same |

TABLE 1-continued

FORMULATION RANGES OF EXEMPLARY COMPONENTS OF COLLECTION COMPOSITIONS

| Reagent | Component Final Concentration Ranges |
|---|---|
| Sodium taurodeoxycholate, or Sodium cholate | Same about 0.1% to about 1% (wt./vol.) |
| 3. A reducing agent, e.g.: | |
| TCEP | about 0.5 mM to about 30 mM |
| or β-ME, DTT, formamide, or DMSO | about 0.05M to about 0.3M |
| 4. A chelator, e.g.: | |
| Sodium citrate | about 0.5 mM to about 50 mM |
| or EDTA, EGTA, HEDTA, DTPA, NTA, or APCA | about 0.01 mM to about 1 mM |
| 5. A buffer (e.g., TRIS, HEPES, MOPS, MES, Bis-Tris, etc.) | about 1 mM to about 1M |
| 6. An acid (e.g., HCl or citric acid) | q.s. to adjust to a pH of about 6 to 7, preferably 6.4 to 6.8 |
| 7. Nuclease-free water | q.s. to desired final volume |
| Optionally one or more of: | |
| 8. A surfactant/defoaming agent, e.g.: | |
| Antifoam A® or Tween® | about 0.0001% to about 0.3% (wt./vol.) |
| 9. An alkanol (e.g., methanol, ethanol, propanol, etc.) | about 1% to about 25% (vol./vol.) |
| 10. RNA or DNA | about 1 pg to about 1 µg/mL |

TABLE 2

FORMULATION RANGES OF EXEMPLARY COMPONENTS OF PCR_READY COMPOSITIONS

| Reagent | Component Final Concentration Ranges |
|---|---|
| 1. One or more buffers, e.g.; Tris, citrate, MES, BES, Bis-Tris, HEPES, MOPS, Bicine, Tricine, ADA, ACES, PIPES, bicarbonate, phosphate | about 1 mM to about 1M |
| 2. One or more polymerase chain reaction osmolarity agents, cationic functionalized zwitterionic compounds, e.g.: betaine, DMSO, foramide, glycerol, nonionic detergents, BSA, polyethylene glycol, tetramethylammonium chloride | about 1 mM to about 1M |
| 3. One or more chelators, e.g.: EGTA, HEDTA, DTPA, NTA, EDTA, citrate anhydrous, sodium citrate, calcium citrate, ammonium citrate, ammonium bicitrate, citric acid, diammonium citrate, potassium citrate, magnesium citrate, ferric ammonium citrate, lithium citrate | about 0.01 mM to about 1 mM |
| 4. One or more dyes, e.g.: fluorescein, 5-carboxy-X-rhodamine, ROX™ | about 0.01 mM to about 50 mM |
| 5. One or more salts, e.g.: potassium chloride, magnesium sulfate, potassium glutamate | about 50 mM to about 1M |
| 6. One or more polymerases, e.g.: Taq, Pfu, KOD, Hot start polymerases, next gen. polymerases | about 0.05 U to about 1 U |
| 7. Deoxynucleoside triphosphates, e.g.: dATP, dTTP, dGTP, dCTP, dUTP | about 0.1 mM to about 1 mM |

TABLE 3

| MTB total DNA (sample 1) | 18.0 |
|---|---|
| MTB total DNA9 (sample 2) | 17.8 |
| MTB RNA only (sample 1) | 21.0 |
| MTB RNA only (sample 2) | 20.8 |

TABLE 3-continued

| HN878 total DNA (positive control) | 18.3 |
|---|---|
| HN878 total DNA (positive control) | 18.2 |
| Pos CTRL | 33.3 |
| Neg CTRL | Undetected |

The invention claimed is:

1. A method of rapidly quantifying microorganisms in a blood sample comprising:

combining the blood sample with a composition to form a mixture, wherein the composition comprises a chaotrope, a detergent, a reducing agent, a chelator and a buffer;

combining at least a portion of the mixture with a PCR-ready composition to form a reaction mixture containing microorganism-specific sequences, wherein the PCR-ready composition comprises as components a heat-stable polymerase; a mix of deoxynucleotide tri phosphates; a pair of PCR primers configured to amplify by PCR a nucleic acid sequence that is specific for the microorganisms; a chelating agent; an osmolarity agent; an albumin; at least two salts at least one of which is a magnesium salt; and a buffer present at a pH of about 6.5 to about 9.0, wherein the pKa of the composition is within about one unit of the pH at a selected temperature, wherein the components are combined with nuclease-free water;

PCR amplifying the microorganism-specific sequences of the reaction mixture to form amplification products; and quantitating the amplification products to determine the quantity of microorganisms present in the blood sample, wherein the time from collection of the sample to quantitation is less than about two days.

2. The method of claim 1, wherein the heat-stable polymerase is a Taq polymerase, a high fidelity polymerase, a Pfu polymerase, a hot start polymerase, or a next gen polymerase.

3. The method of claim 1, wherein composition further comprises a dye.

4. The method of claim 3, wherein the dye is selected from the group consisting of fluorescein, 5-carboxy-X-rhodamine and ROX.

5. The method of claim 1, wherein the pH of the composition is from about 6.5 to about 7.5 and the pKa is within 0.5 of the pH of the buffer at ambient temperature.

6. The method of claim 5, wherein the pKa of the composition is within 0.2 of the pH of the buffer at ambient temperature.

7. The method of claim 1, wherein the PCR-ready composition has a pH from about 6.5 to 7.0.

8. The method of claim 7, wherein the pair of PCR primers are each from about 18 to 35 nucleotides in length.

9. The method of claim 1, wherein the microorganisms are bacteria, virus, fungi, parasites or combinations thereof.

10. The method of claim 9, wherein the bacteria are MTB, the virus is HIV, or the parasites is a *Plasmodium* species and/or *Plasmodium falciparum*.

11. The method of claim 1, further comprising a control nucleic acid present in the PCR-ready composition at a concentration of about 1 fg to about 1 ng.

12. The method of claim 1, wherein the time from collection of the sample to quantitation is less than about one day.

13. The method of claim 1, wherein the time from collection of the sample to quantitation is less than about 12 hours.

14. A high throughput method for rapidly quantitating amplification products to determine the quantity of microorganisms present in multiple blood samples comprising repeated cycles of the method of claim 1.

15. A method for rapidly quantifying multiple different microorganisms in a biological sample containing nucleic acid comprising:
 contacting the biological sample with a transport composition comprising a chaotrope, a detergent, a reducing agent, a chelator and a buffer;
 combining the nucleic acid of the biological sample with pairs of PCR primer sequences that are specific to each different microorganism and a PCR-ready composition to form a reaction mixture, wherein the PCR-ready composition comprises as components a heat-stable polymerase; a mix of deoxynucleotide tri phosphates; a chelating agent; an osmolarity agent; an albumin; at least two salts at least one of which is a magnesium salt; and a buffer present at a pH of about 6.5 to about 9.0, wherein the components are combined with nuclease-free water;
 performing PCR on the reaction mixture to form amplification products that are specific for each of the different microorganisms;
 detecting the quantity of each amplification product; and
 determining the quantity of each microorganism in the sample, wherein the time from collection of the sample to determining the quantity of each microorganism is less than about two days.

16. The method of claim 15, wherein each amplification product is compared with a control nucleic acid to determine the quantity of each microorganism in the sample.

17. The method of claim 15, wherein the quantity of each amplification product provides a measure of the severity or level of infection attributable to each of said different microorganisms.

18. The method of claim 15, wherein the biological sample is obtained from an individual and the quantity of each amplification product provides a measure of the disease state of the individual attributable to each of said different microorganisms.

19. A high throughput method for rapidly determining the quantity of each microorganism in the sample comprising the method of claim 15.

20. A method of tracking the progression of an infectious disease of an individual wherein the infectious disease is attributable to a microorganism comprising:
 obtaining multiple blood samples from the individual over a period of time;
 combining at least a portion of nucleic acid of each blood sample with pairs of PCR primer sequences that are specific to the microorganism and a PCR-ready composition to form a reaction mixture, wherein the PCR-ready composition comprises a heat-stable polymerase; a mix of deoxynucleotide tri phosphates; a chelating agent; an osmolarity agent; an albumin; at least two salts at least one of which is a magnesium salt; and a buffer present at a pH of about 6.5 to about 9.0, wherein the components are combined with nuclease-free water;
 performing PCR on the reaction mixture to form amplification products that are specific for the microorganism;
 detecting the quantity of microorganisms present in each sample; and
 determining the progression of the infection disease of the individual.

21. The method of claim 20, wherein the individual has multiple infections attributable to multiple microorganisms and tracking the progression of each infectious disease.

22. The method of claim 21, wherein the multiple infections include at least two of MTB, *Plasmodium* and HIV.

23. A high throughput method for rapidly determining the severity, progression or resolution of the infectious disease of the individual comprising the method of claim 20.

24. A kit comprising the collection and PCR-Ready compositions of claim 1, each contained within a sterile vessel configured for addition of a biological sample and thermal cycling, and instructions for determining the presence or absence of a pathogen from the results of the thermal cycling.

25. A method for rapidly determining the development of an infection of an individual comprising:
 contacting each of multiple biological samples collected from the individual suspected of containing an infectious microorganism over multiple periods of time with a composition to form multiple reaction mixtures, wherein each reaction mixture represents one of the multiple periods of time and the composition comprises a chaotrope, a detergent, a reducing agent, a chelator and a buffer;
 separately combining a portion of each reaction mixture with a PCR-ready composition containing at least a reverse transcriptase to convert mRNA sequences of the infectious microorganism to DNA sequences, a heat-stable polymerase; a mix of deoxynucleotide tri phosphates, a chelating agent, an osmolarity agent, an albumin, at least two salts at least one of which is a magnesium salt, and a buffer present at a pH of about 6.5 to about 9.0, which are combined with nuclease-free water;

performing a PCR on each reaction mixture to produce amplification products of the DNA sequences of the infectious microorganism and amplification products of a genomic sequence of the individual;

detecting the quantity and/or ratio of the amplification products of the DNA sequences and the amplification products of the genomic sequence in each reaction mixture; and determining a ratio of amplification products from the DNA sequences and amplification products from genomic sequences to determine the development of the infection.

26. The method of claim 25, wherein the infection is bacterial, viral, fungal, parasitic, or a combination thereof.

27. The method of claim 26, wherein the bacterial infection is Mycobacteria tuberculosis.

28. The method of claim 26, wherein the viral infection is influenza virus, HIV or Zika virus.

29. The method of claim 26, wherein the parasitic infection is *Plasmodium falciparum*.

30. The method of claim 25, wherein the multiple biological samples comprise blood, serum, sputum, saliva, nasal discharge, biopsied material, or skin scraping.

31. The method of claim 25, the multiple periods of time comprise hours, days or weeks.

32. The method of claim 25, wherein a decrease in the quantity or ratio of amplification products of the DNA sequences as compared to the amplification products of the genomic sequences over time indicates a reduction of the development of the infection and an increase in the quantity or ratio of amplification products of the DNA sequences as compared to the amplification products of the genomic sequences over time indicates an increase of the development of the infection.

33. The method of claim 25, further comprising administering a pharmaceutical agent to the individual.

34. The method of claim 33, wherein the pharmaceutical agent is an antibody, a drug, an antibiotic, a natural product, a manufactured product, an antimicrobial agent, a placebo or a combination thereof.

35. The method of claim 1, wherein the composition denatures proteins, inactivates nucleases, and kills pathogens, and does not interfere with the PCR amplifying.

36. The method of claim 15, wherein the composition denatures proteins, inactivates nucleases, and kills pathogens, and does not interfere with the PCR.

37. The method of claim 25, wherein the composition denatures proteins, inactivates nucleases, and kills pathogens, and does not interfere with the PCR.

* * * * *